United States Patent [19]

Doehner, Jr.

[11] Patent Number: 5,300,479
[45] Date of Patent: Apr. 5, 1994

[54] HERBICIDAL 2-(2-IMIDAZOLIN-2-YL)-BENZTRIAZOLES

[75] Inventor: Robert F. Doehner, Jr., East Windsor, N.J.

[73] Assignee: American Cyanamid Company, Wayne, N.J.

[21] Appl. No.: 874,446

[22] Filed: Apr. 27, 1992

Related U.S. Application Data

[62] Division of Ser. No. 576,621, Aug. 31, 1990, Pat. No. 5,108,485.

[51] Int. Cl.$^5$ ............................................ C07D 249/18
[52] U.S. Cl. ...................................... 504/261; 548/261
[58] Field of Search ..................... 548/261; 71/92; 504/261

[56] References Cited

U.S. PATENT DOCUMENTS

| | | | |
|---|---|---|---|
| 4,188,487 | 2/1980 | Los | 71/92 |
| 4,297,128 | 10/1981 | Los | 71/92 |
| 4,554,013 | 11/1985 | Los | 71/92 |
| 4,608,079 | 8/1986 | Los | 548/301 |
| 4,614,535 | 9/1986 | Schmiener | 548/301 |
| 4,623,380 | 11/1986 | Schmier | 71/92 |
| 4,650,514 | 3/1987 | Los | 71/92 |
| 4,721,522 | 1/1988 | Durr | 71/92 |
| 4,752,323 | 6/1988 | Los et al. | 71/92 |
| 4,758,667 | 7/1988 | Szczepanski | 546/278 |
| 4,767,444 | 8/1988 | Hewang | 71/92 |
| 4,785,002 | 11/1988 | Draber | 71/92 |
| 4,824,474 | 4/1989 | Numata | 71/92 |
| 4,859,684 | 8/1989 | Raemaekers | 548/327 |
| 4,895,588 | 1/1990 | Dingwall | 71/92 |
| 4,911,747 | 3/1990 | Los | 548/301 |
| 4,943,574 | 7/1990 | Raeymaekers et al. | 548/261 |
| 4,959,476 | 9/1990 | doehner | 548/301 |
| 5,066,656 | 11/1991 | Greco | 548/261 |
| 5,108,485 | 4/1992 | Doehner et al. | 71/92 |
| 5,116,403 | 5/1992 | Bhalla et al. | 71/92 |

FOREIGN PATENT DOCUMENTS 198522 10/1986 European Pat. Off. .
2172886A 10/1986 United Kingdom .

OTHER PUBLICATIONS

R. L. Williams et al., Journal of Heterocyclic Chemistry, 1973, (10), 891.

Primary Examiner—Donald G. Daus
Attorney, Agent, or Firm—John W. Hogan, Jr.

[57] ABSTRACT

There are provided o-carboxy-(5-oxo-2-imidazolin-2-yl)benzoheterocyclic compounds wherein the fused heterocyclic ring system is a 5-membered ring containing one, two or three nitrogen atoms, derivatives of said benzoheterocyclic compounds and a method for the use therewith to control monocotyledenous and dicotyledenous plant species.

11 Claims, No Drawings

HERBICIDAL 2-(2-IMIDAZOLIN-2-YL)-BENZTRIAZOLES

This is a divisional of co-pending application Ser. No. 07/576,621, filed on Aug. 31, 1990 now U.S. Pat. No. 5,108,485.

BACKGROUND OF THE INVENTION

Certain imidazolinyl benzoic and naphthoic acids, esters and salts and their use as herbicidal agents are described in U.S. Pat. Nos. 4,188,487; 4,297,128 and 4,554,013 and in patent applications GB 2 172 866 A and EP 86200304.3. However, the imidazolinyl benzazoles of the present invention are not described nor suggested in said patents and patent applications. Fused heteropyridine compounds and their herbicidal use are described in U.S. Pat. Nos. 4,650,514 and 4,752,323 and copending U.S. application Ser. No. 465,569 filed on Jan. 16, 1990. Although a variety of herbicidally active imidazolinyl compounds are known, still more effective imidazolinyl compounds would be useful to farmers, agriculturalists, industrialists and the like for the control of undesirable plant species.

It is an object of the present invention to provide effective herbicidal imidazolinyl o-carboxy-2-benzoheterocyclic compounds and indoloheterocyclic diones for controlling a variety of monocotyledenous and dicotyledenous plant species such as those species which are generally difficult to control in agronomic practice.

SUMMARY OF THE INVENTION

The present invention relates to 2-(2-imidazolin-2-yl)benzoheterocyclic compounds having the structure

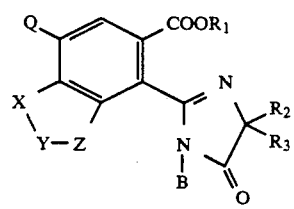 a.

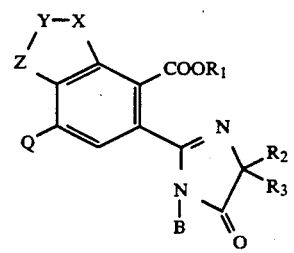 b.

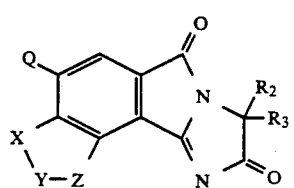 c.

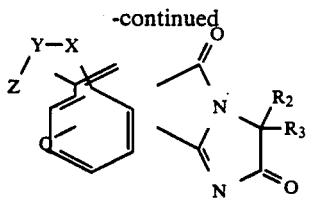 d.

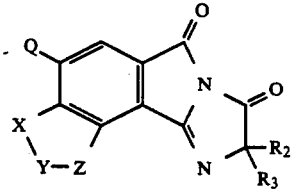 e.

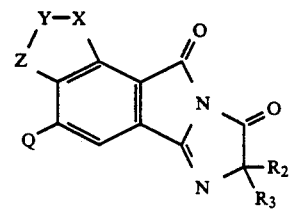 f.

wherein $R_1$ is hydrogen, di($C_1$-$C_4$)alkylimino,
$C_1$-$C_{12}$ alkyl options substituted with one to three of the following: $C_1$-$C_4$ alkoxy, $C_1$-$C_4$ alkylthio, halogen, hydroxy, $C_3$-$C_6$ cycloalkyl, benzyloxy, furyl, phenyl optionally substituted with one nitro, one to three halogens, $C_1$-$C_4$ alkyl groups or $C_1$-$C_4$ alkoxy groups, carboxy, $C_1$-$C_4$ alkoxycarbonyl, cyano or tri($C_1$-$C_4$) alkylammonium halide,
$C_3$-$C_{12}$ alkenyl optionally substituted with one to three of the following: $C_1$-$C_4$ alkoxy, phenyl, halogen or $C_1$-$C_4$ alkoxycarbonyl,
$C_3$-$C_6$ cycloalkyl optionally substituted with one to three $C_1$-$C_4$ alkyl groups,
$C_3$-$C_{16}$ alkynyl optionally substituted with one to three halogens or a cation;
$R_2$ is $C_1$-$C_4$ alkyl;
$R_3$ is $C_1$-$C_4$ alkyl or $C_3$-$C_6$ cycloalkyl, and when $R_2$ and $R_3$ are taken together with the carbon to which they are attached they may represent $C_3$-$C_6$ cycloalkyl optionally substituted with methyl;
B is hydrogen, $COR_4$ or $SO_2R_5$ with the proviso that when B is $COR_4$ or $SO_2R_5$, $R_1$ is other than hydrogen or a cation and $R_9$ is other than hydrogen;
$R_4$ is $C_1$-$C_{11}$ alkyl, chloromethyl or phenyl optionally substituted with halogen, nitro or $C_1$-$C_4$ alkyl;
$R_5$ is $C_1$-$C_4$ alkyl or phenyl optionally substituted with $C_1$-$C_4$ alkyl;
X, Y and Z are each independently $CR_6$, $CR_7R_8$, N or $NR_9$, with the proviso that at least one of X, Y and Z must be N or $NR_9$;
the ─── configuration represents either a single bond or a double bond with the proviso that when any of X, Y or Z is $CR_7R_8$ or $NR_9$, then the ─── configuration attached thereto is a single bond and with the further proviso that at least one of the ─── configuration represents a single bond;
$R_6$, $R_7$ and $R_8$ are independently hydrogen, halogen, $C_1$-$C_4$ alkoxy or $C_1$-$C_4$ alkyl optionally substituted with one hydroxy or one to three halogens, $C_1$-$C_4$ alkoxy groups or $C_1$-$C_4$ alkylthio groups;

$R_9$ is hydrogen or $C_1$-$C_4$ alkyl optionally substituted with one hydroxy or one to three halogens, $C_1$-$C_4$ alkoxy groups or $C_1$-$C_4$ alkylthio groups;

Q is hydrogen, halogen, $C_1$-$C_4$ alkoxy or $C_1$-$C_4$ alkyl optionally substituted with one to three of the following: halogen, $C_1$-$C_4$ alkoxy, $C_1$-$C_4$ alkylthio or $C_2$-$C_4$ alkenyl;

the optical isomer thereof when $R_2$ and $R_3$ are not the same or when $R_7$ and $R_8$ are not the same;

the tautomers and geometric isomers thereof and the acid addition salts thereof except when $R_1$ is a salt-forming cation.

The present invention further provides processes for the preparation of the above-said compounds and methods for controlling undesirable monocotyledenous and dicotyledenous plant species therewith.

Related benzoheterocyclic compounds and their herbicidal use are described in co-pending patent application, Ser. Nos. 07/576,643 and 07/576,645, filed concurrently herewith and incorporated herein by reference thereto, now U.S. Pat. Nos. 5,283,335 and 5,180,419.

DESCRIPTION OF THE INVENTION

This invention relates to 2-(2-imidazolin-2-yl)benzoheterocyclic compounds having the structure

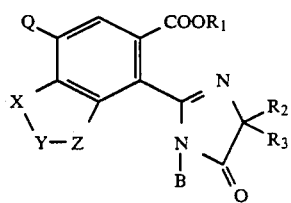 a.

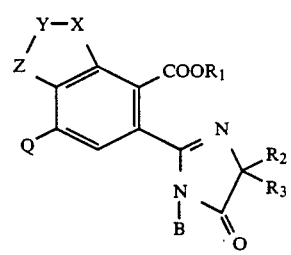 b.

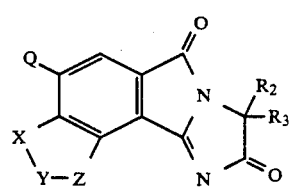 c.

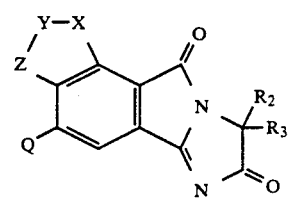 d.

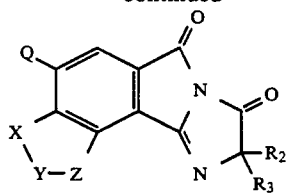 e.

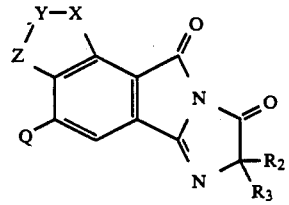 f.

wherein $R_1$ is hydrogen, di($C_1$-$C_4$)alkylimino, $C_1$-$C_{12}$ alkyl optionally substituted with one to three of the following: $C_1$-$C_4$ alkoxy, $C_1$-$C_4$ alkylthio, halogen, hydroxy, $C_3$-$C_6$ cycloalkyl, benzyloxy, furyl, phenyl, optionally substituted with one nitro, one to three halogens, $C_1$-$C_4$ alkyl groups or $C_1$-$C_4$ alkoxy groups, carboxy, $C_1$-$C_4$ alkoxycarbonyl, cyano or tri($C_1$-$C_4$)alkylammonium halide, $C_3$-$C_{12}$ alkenyl optionally substituted with one to three of the following: $C_1$-$C_4$ alkoxy, phenyl, halogen or $C_1$-$C_4$ alkoxycarbonyl, $C_3$-$C_6$ cycloalkyl optionally substituted with one to three $C_1$-$C_4$ alkyl groups, $C_3$-$C_{16}$ alkynyl optionally substituted with one to three halogens or a cation;

$R_2$ is $C_1$-$C_4$ alkyl;

$R_3$ is $C_1$-$C_4$ alkyl or $C_3$-$C_6$ cycloalkyl, and when $R_2$ and $R_3$ are taken together with the carbon to which they are attached they may represent $C_3$-$C_6$ cycloalkyl optionally substituted with methyl;

B is hydrogen, $COR_4$ or $SO_2R_5$ with the proviso that when B is $COR_4$ or $SO_2R_5$, $R_1$ is other than hydrogen or a cation and $R_9$ is other than hydrogen;

$R_4$ is $C_1$-$C_{11}$ alkyl, chloromethyl or phenyl optionally substituted with halogen, nitro or $C_1$-$C_4$ alkyl;

$R_5$ is $C_1$-$C_4$ alkyl or phenyl optionally substituted with $C_1$-$C_4$ alkyl;

X, Y and Z are each independently $CR_6$, $CR_7R_8$, $NR_9$ or N with the proviso that at least one of X, Y or Z is N or $NR_9$;

the ═ configuration represents either a single bond or a double bond with the proviso that when any of X, Y or Z is $CR_7R_8$ or $NR_9$, then the ═ configuration attached thereto represents a single bond and with the further proviso that at least one of the ═ configuration represents a single bond;

$R_6$, $R_7$ and $R_8$ are independently hydrogen, halogen, $C_1$-$C_4$ alkoxy or $C_1$-$C_4$ alkyl optionally substituted with one hydroxy or one to three halogens, $C_1$-$C_4$ alkoxy groups or $C_1$-$C_4$ alkylthio groups;

$R_9$ is hydrogen or $C_1$-$C_4$ alkyl optionally substituted with one hydroxy or one to three halogens, $C_1$-$C_4$ alkoxy groups or $C_1$-$C_4$ alkylthio groups;

Q is hydrogen, halogen, $C_1$-$C_4$ alkoxy or $C_1$-$C_4$ alkyl optionally substituted with one to three of the following: halogen, $C_1$-$C_4$ alkoxy, $C_1$-$C_4$ alkylthio or $C_2$-$C_4$ alkenyl;

the optical isomers thereof when $R_2$ and $R_3$ are not the same or when $R_7$ and $R_8$ are not the same;

the tautomers and geometric isomers thereof and the acid addition salts thereof except when $R_1$ is a salt-forming cation.

The term halogen designates F, Cl, Br or I. The term cation, as used in the present specification and claims, designates alkali metals, alkaline earth metals, manganese, copper, iron, zinc, cobalt, lead, silver, nickel, ammonium or organic ammonium. The alkali metals include sodium, potassium and lithium. Among the organic ammonium cations suitable for use in the present invention are monoalkylammonium, dialkyl ammonium, trialkylammonium, tetraalkylammonium, monoalkenylammonium, dialkenylammonium, trialkenylammonium, monoalkynylammonium, dialkynylammonium, monoalkanolammonium, dialkanolammonium, $C_5$-$C_6$ cycloalkylammonium, piperidinium, morpholinium, pyrrolidinium, benzylammonium and the like.

Among the o-carboxy-(5-oxo-2-imidazolin-2-yl)benzoheterocycles described in the present invention are o-(2-imidazolin-2-yl)indolecarboxylates, o-(2-imidazolin-2-yl)indazolecarboxylates, o-(2-imidazolin-2-yl)benzimidazolecarboxylates, o-(2-imidazolin-2-yl)benzotriazole carboxylates, and the like.

Herbicidally active imidazolinyl benzoheterocyclic compounds having the structure

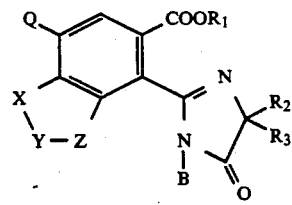

a.

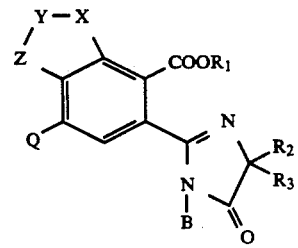

b.

wherein B is hydrogen and $R_1$, $R_2$, $R_3$, X, Y, Z and Q are as described hereinabove can be prepared from their imide nitrile precursors having the structure of formula I.

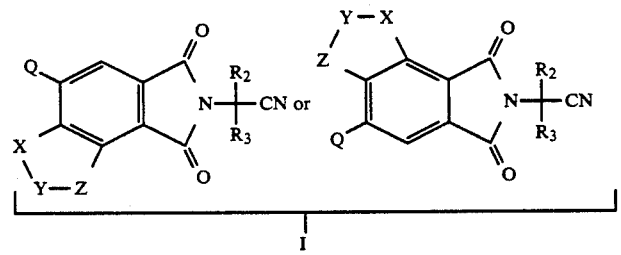

I

There is a recognized need in agronomic practice for still more effective herbicidal agents and, especially, effective herbicidal agents which can be used in the presence of important agricultural crops without causing undue injury to said crops. Without adequate control, undesirable plant species can eliminate or reduce the yield of crops, reduce the quality and value of crops and reduce the efficient production and harvest of crops. The herbicidal imidazolinyl benzoheterocycles of the present invention exhibit effective control of a wide variety of undesirable monotyledenous and dicotyledenous plant species and, moreover, demonstrate good selectivity towards important broadleaf crops such as soybeans and sugarbeets.

The nitrile groups on the formula I compounds can be hydrolyzed in the presence of sulfuric acid to give the corresponding amides and the resultant imide amides ring opened in the presence of an appropriate nucleophile such as an alkali metal alkoxide to give the ester diamide intermediates of formula II and their regioisomers. The formula II ester diamides can be converted to the desired compounds having structure a or b by reaction with phosphorous pentachloride in the presence of a solvent. In the case wherein $R_6$, $R_7$, $R_8$ or $R_9$ contain one or more hydroxy groups, these hydroxy groups are converted to chloro groups by this reaction. The reaction sequence is illustrated in flow diagram I.

FLOW DIAGRAM I

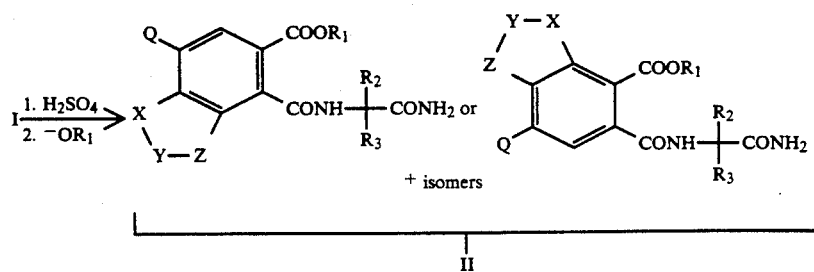

II

FLOW DIAGRAM I

-continued

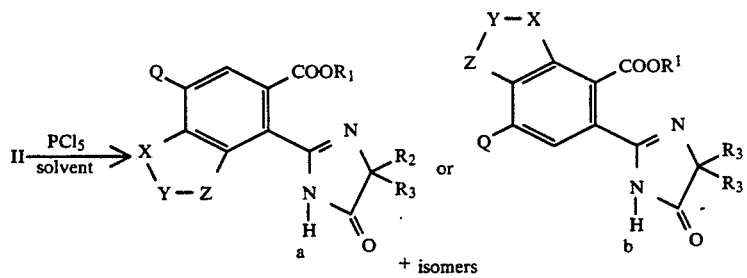
+ isomers

The regioisomers can be separated by standard chromatographic techniques such as reverse phase liquid chromatography.

Alternatively, compounds having structure a or b as described hereinabove and wherein $R_1$ is hydrogen can be prepared in 2 steps by reacting the appropriate phthalic anhydride with an amino amide of formula III in the presence of a base such as triethylamine, and optionally in the presence of a solvent, to obtain the corresponding acid diamide intermediates and their regioisomers and ring closing said intermediates in an aqueous alkali metal base followed by acidification to give the desired o-2(imidazolin-2-yl)benzoheterocyclic carboxylic acids having structure a or b and their regioisomers as shown in flow diagram II.

FLOW DIAGRAM II

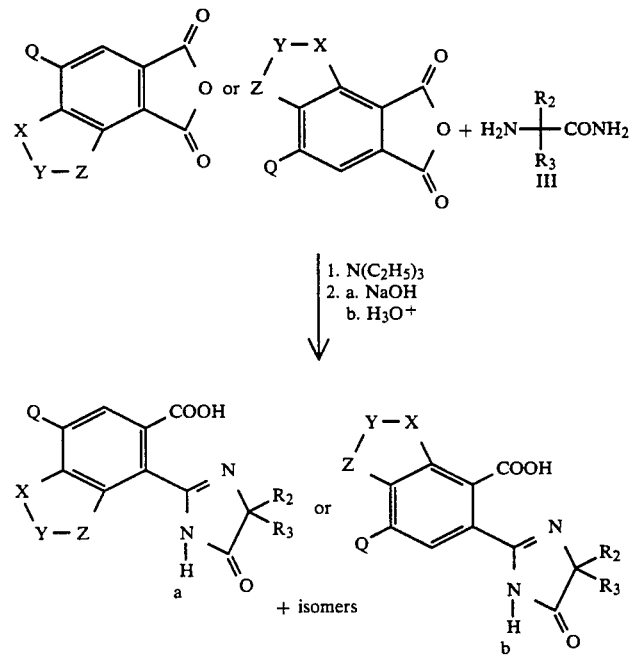
+ isomers

The regioisomers can be separated using standard chromatographic techniques such as reverse phase liquid chromatography.

Another method of preparing compounds of structure a or b as described hereinabove wherein $R_1$ and B are hydrogen is similar to that described in U.S. Pat. No. 4,758,667 wherein a diester of formula IV is treated with an alkali metal alkoxide such as potassium t-butoxide and an aminoamide of formula III in the presence of an inert solvent such as xylene and sequentially treated with an aqueous acid to give the desired imidazolinyl benzoheterocycles as shown in flow diagram III wherein $R_{10}$ is $C_1$-$C_8$ alkyl.

FLOW DIAGRAM III

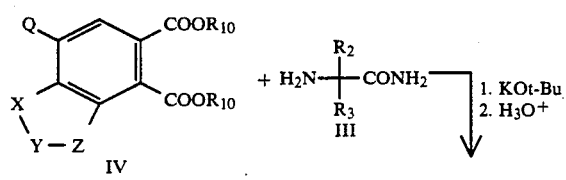

FLOW DIAGRAM III

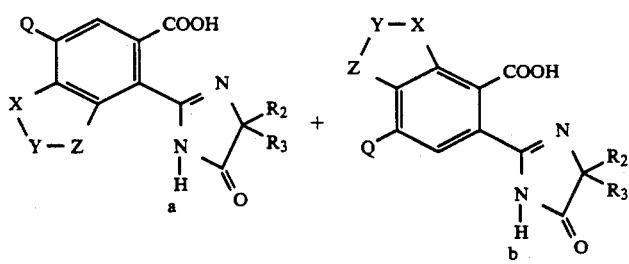

Compounds having structure c and d can be prepared from the appropriate imide nitriles of formula I by the acid hydrolysis of the nitrile groups to give the corresponding imide amides and the cyclization thereof in the presence of an alkali metal hydride such as sodium hydride to give the desired indoloheterocyclic diones as shown in flow diagram IV.

FLOW DIAGRAM IV

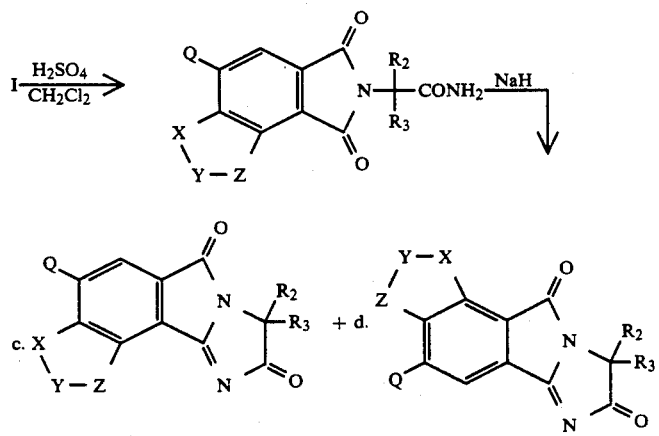

Compounds having structure a or b wherein $R_1$ is other than hydrogen and B is hydrogen may be prepared from compounds having structure c or d by reacting said compounds with an appropriate nucleophile such as an alkali metal alkoxide as shown in flow diagram V.

FLOW DIAGRAM V

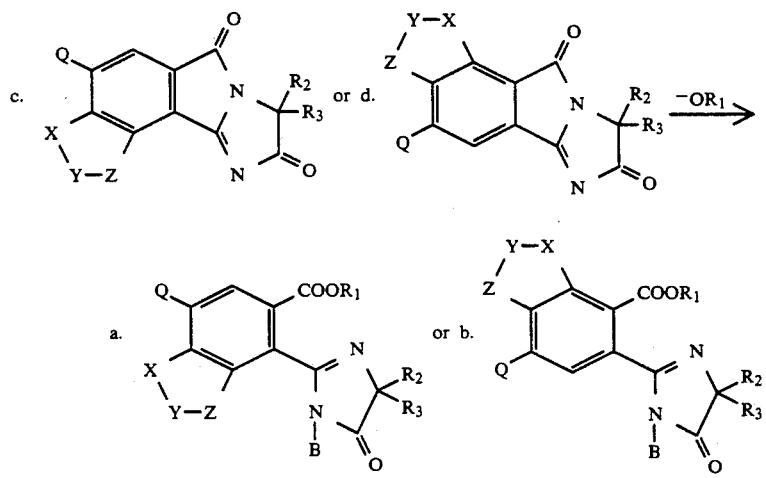

Compounds having structure e or f can be prepared by reacting the o-(2-imidazolin-2-yl)benzoheterocyclic carboxylic acids having structure a or b wherein B is hydrogen with dicyclohexylcarbodiimide (DCC) in the presence of a non-protic solvent as shown in flow diagram VI.

FLOW DIAGRAM VI

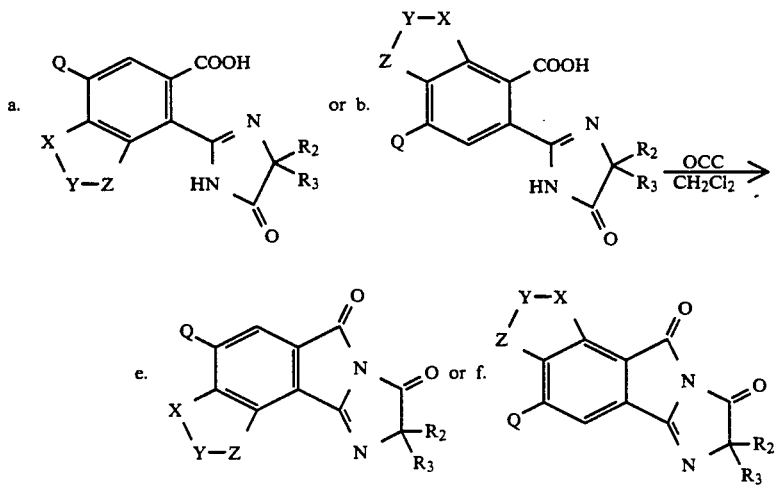

Compounds of structure c and d wherein Z is $NR_9$ or N, X and Y are CH and Q is hydrogen can be prepared illustrated in flow diagram IV. The reaction scheme is shown below in flow diagram VII.

FLOW DIAGRAM VII

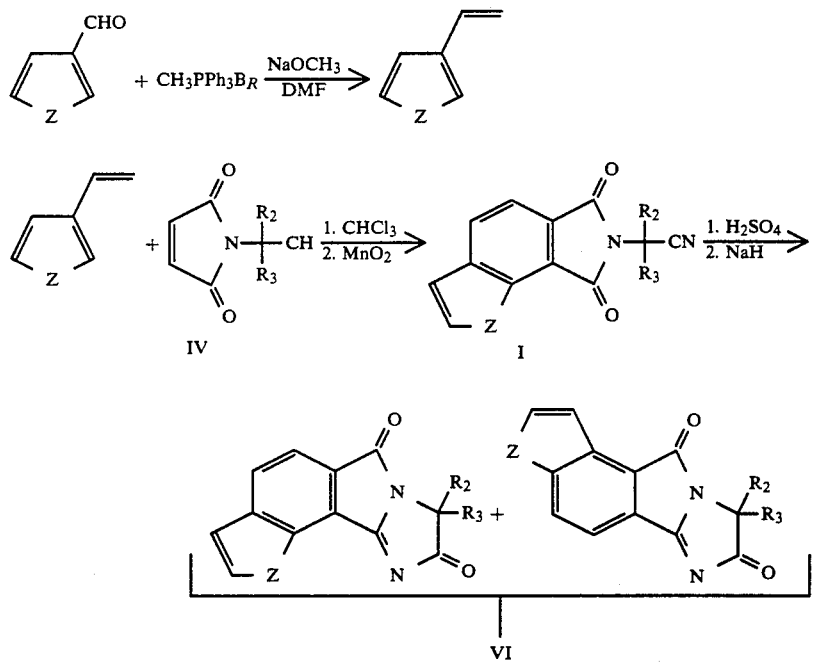

from the appropriate 3-vinylpyrrole by the formation of the corresponding imide nitrile intermediate of formula I via a Diels-Alder reaction with a suitably substituted maleimide nitrile of formula V, followed by oxidation using an oxidizing reagent conventional in the art such as manganese dioxide to achieve the desired oxidation state. Formation of the 3-vinylpyrrole starting material is accomplished via a Wittig reaction. The thus-formed imide nitrile intermediate of formula I can be converted to the desired indoloheterocyclic diones of formula VI by the reaction sequence described hereinabove and And as described hereinabove, the formula VI diones may be converted to the corresponding imidazolinyl benzoheterocycles of structures a and b as shown in flow diagram V wherein Z is $NR_9$ or N, X and Y are $CH_2$ and B and Q are hydrogen.

Similarly, compounds having structures a, b, c and d wherein X is $NR_9$ or N, Y and Z are $CH_2$ and B and Q are hydrogen can be prepared from 2-pyrrolecarboxaldehyde by repeating the reaction sequence shown in flow diagrams VII and V, respectively as shown below.

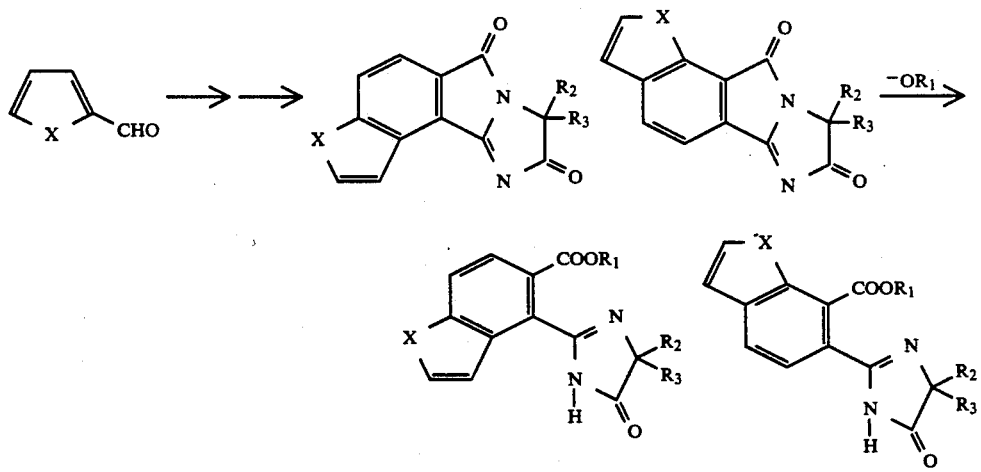

Compounds having structure a wherein X and Y are N or NR$_9$, Z is CR$_6$ and B and Q are hydrogen are prepared from 2-keto-1,3-cyclohexanedione in the following manner: condensation of said dione with the appropriately substituted hydrazine affords the 1,3-disubstituted-dihydroindazolone of formula VII; treatment of the formula VII intermediate with sodium hydride and ethyl carbonate gives the tetrahydroindazole-5-carboxylate of formula VIII; treatment of the formula VIII ketone with trimethylsilyl cyanide and zinc iodide followed by deprotection/dehydration gives the dihydro-4-cyanoindazole-5-carboxylate of formula IX; dehydrogenation of the formula IX compound and subsequent treatment of the reaction product with hydrogen bromide and acetic acid yields 1,3-dimethyl-1H-indazole-4,5-dicarboxylic acid; acetic anhydride treatment affords the corresponding anhydride which can be regiospecifically ring opened with the appropriate formula III aminoamide and converted to the desired imidazolinyl benzoheterocycle having structure a as demonstrated in flow diagram II. The reaction sequence is illustrated in flow diagram VIII.

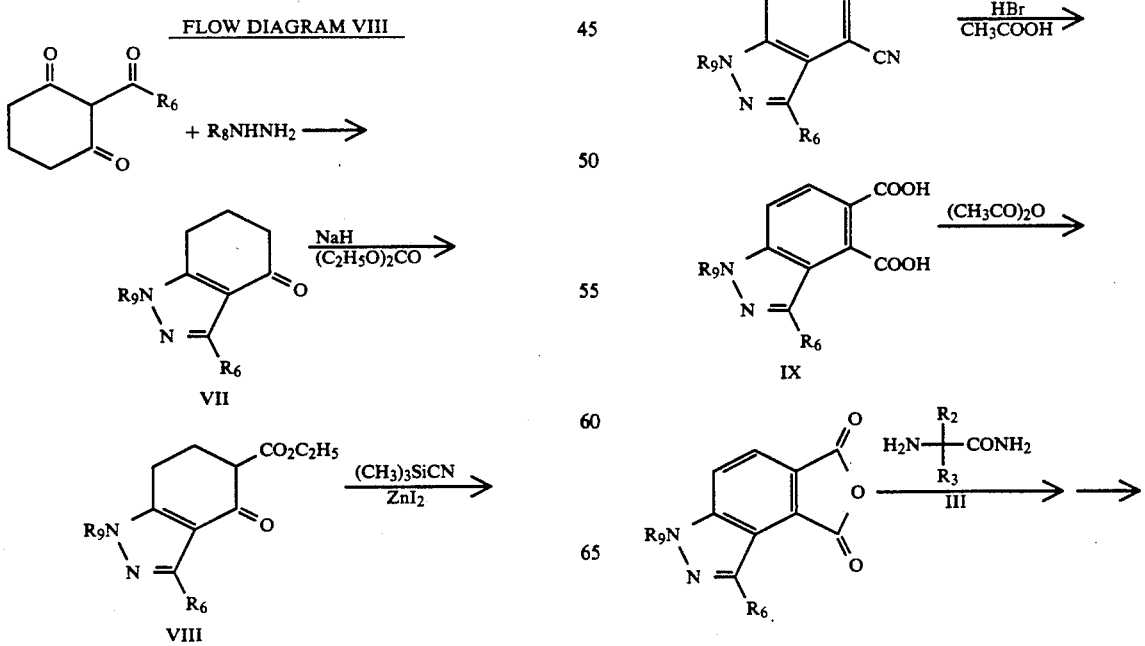

-continued
FLOW DIAGRAM VIII

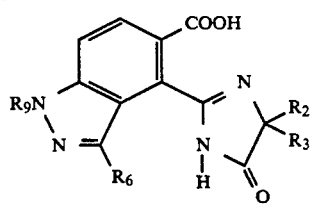

Imidazolinyl indazoles having structure b wherein X is $CR_6$ and Y and Z are N or $NR_9$ can be prepared from the diketal of the appropriately substituted ketoacetaldehyde as shown in flow diagram IX.

FLOW DIAGRAM IX

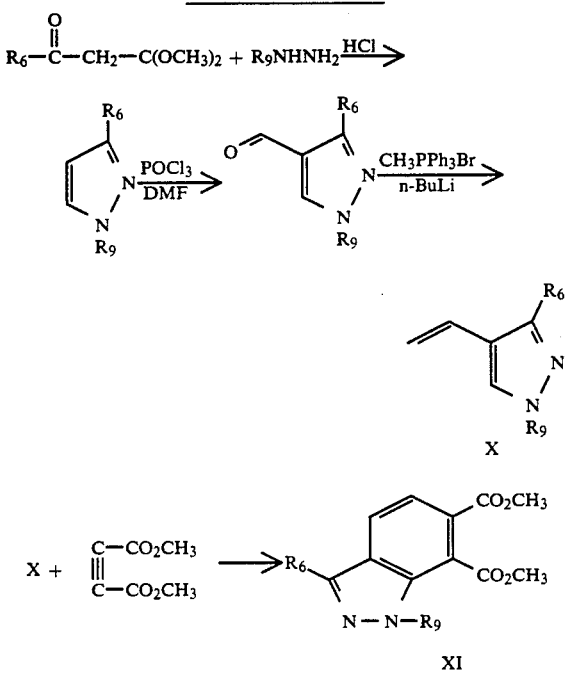

-continued
FLOW DIAGRAM IX

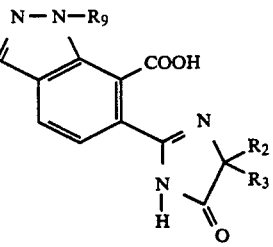

Condensation of the dimethyl acetal of an appropriately substituted ketoacetaldehyde with a suitable hydrazine followed by acid treatment gives the 1,5-disubstituted pyrazole as shown. Treatment of said pyrazole with phosphorus oxychloride and dimethyl formamide (DMF) followed by a Wittig reaction affords the formula X vinylpyrazole. Diels-Alder reaction of the formula X pyrazole with dimethyl acetylenedicarboxylate gives the desired formula XI diester which can then be converted to the imidazolinyl indazole product using the procedure illustrated in flow diagram III.

o-Imidazolinyl benzimidazolecarboxylates having structure a and b can be prepared from their common precursor, a 4-carboxamidophthalate, which is derived from the acylation of 4-aminophthalate. Using the nitration procedure described by R. L. Williams and S. W. Shalaby in the Journal of Heterocyclic Chemistry, 1973, (10), 891 affords the intermediates of formula XII and XIII. Separation of compounds XII and XIII is accomplished via fractional recrystallization. Hydrogenation of compound XIII followed by cyclization of the resultant amidoaniline gives the benzimidazole dicarboxylate of formula XIV. The formula XIV diester can be converted directly to the imidazolinyl benzimidazoles of structures a and b using the methods as described hereinabove and illustrated in flow diagrams II and III. Alternatively, the formula XIV diester can be alkylated with a suitable alkylhalide to give the benzimidazoledicarboxylate of formula XV which is converted to the desired imidazolinyl benzimidazole having structure a and b in the manner shown in flow diagrams II and III. The reaction sequence starting with the appropriate 4-carboxamidophthalate is shown in flow diagram X.

FLOW DIAGRAM X

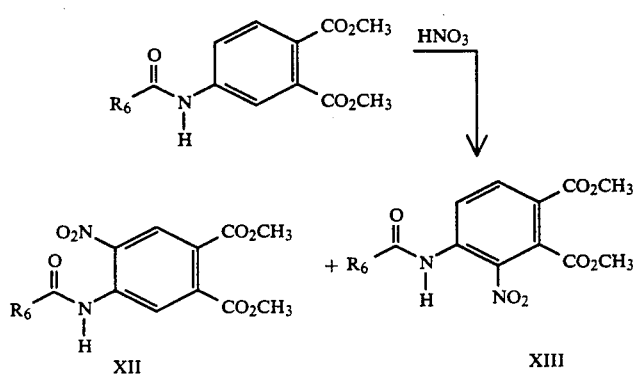

FLOW DIAGRAM X -continued

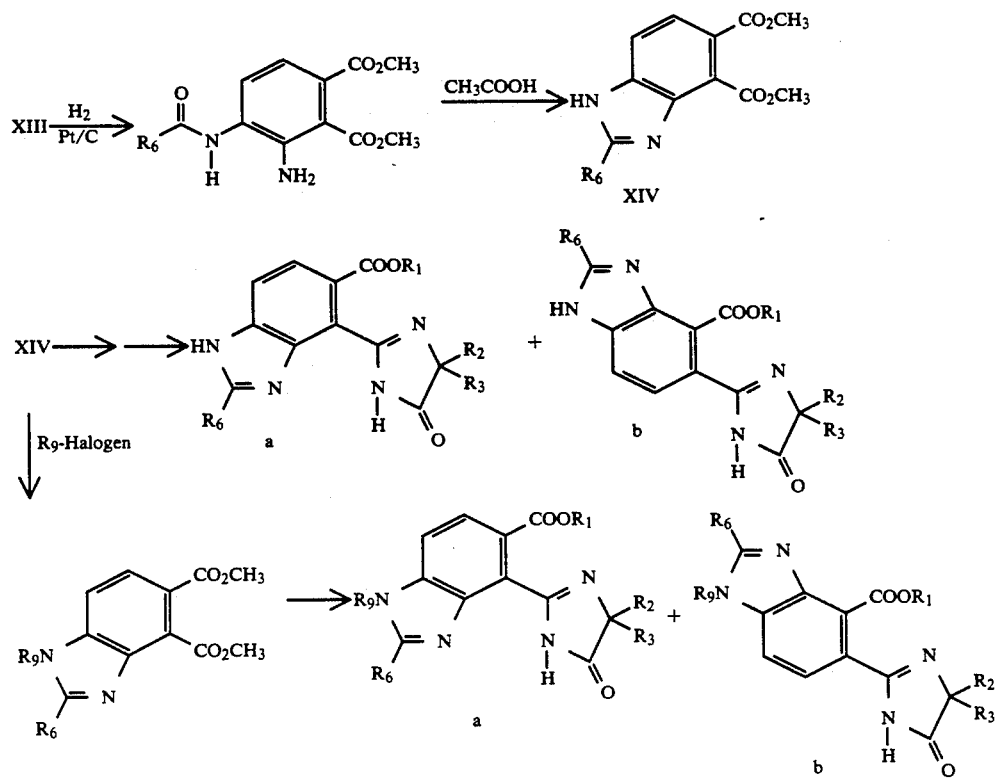

Similarly, the intermediate of formula XII can be converted to the o-imidazolinylbenzimidazole carboxylates of formulas XVI and XVII as shown in flow diagram XI.

hydrogenation to give the diamine of formula XVIII. Treatment of the diamine with formic acid and azeotropic removal of water affords the benzimidazole dicarboxylate of formula XIX which is then directly con-

FLOW DIAGRAM XI

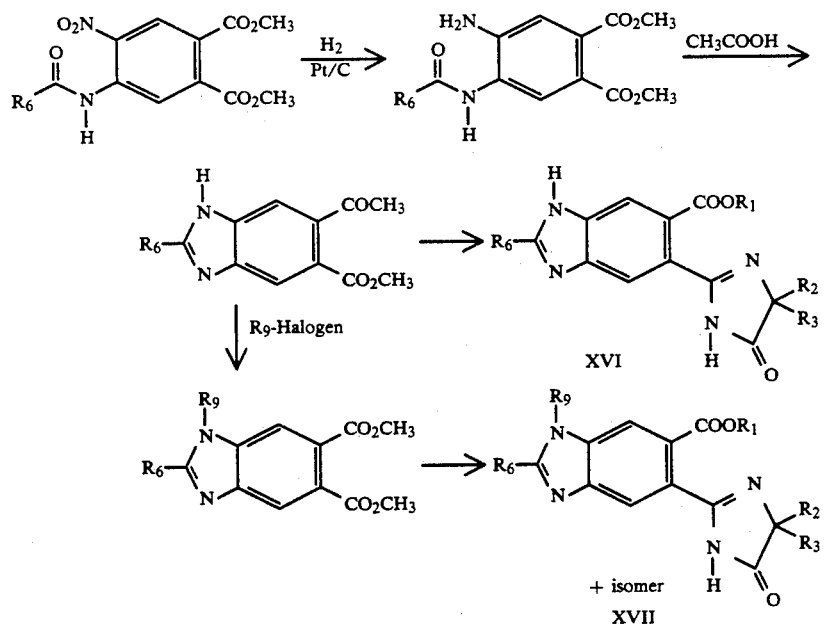

Imidazolinyl benzimidazole compounds wherein $R_6$ is hydrogen can be prepared from compounds of formula XIII by the sequential acid hydrolysis of the amide group and the reduction of the nitro group via catalytic verted to the desired compounds having structure a or b wherein X and Z are N and Y is CH or the formula XVIII diester is alkylated as shown above and the substituted benzimidazole dicarboxylate is converted to the desired compounds having structure a or b wherein X and Z are N or NR₉ and Y is CH. The conversions of the dicarboxylates to the final imidazolinyl benzimidazole compounds is shown in flow diagrams II and III, and the reaction sequence starting with compounds of formula XIII is shown below in flow diagram XII.

Compounds of the invention having structures a and b wherein X, Y and Z are independently N or NR₉ are prepared using the diamine of formula XVIII. Reaction of said diamine with isoamyl nitrite in the presence of acetic acid affords the benzotriazole diester of formula XX which is then converted to the desired compounds having structure a and b wherein X, Y and Z are N or NR₉ in the manner described hereinabove for the benz-

FLOW DIAGRAM XII

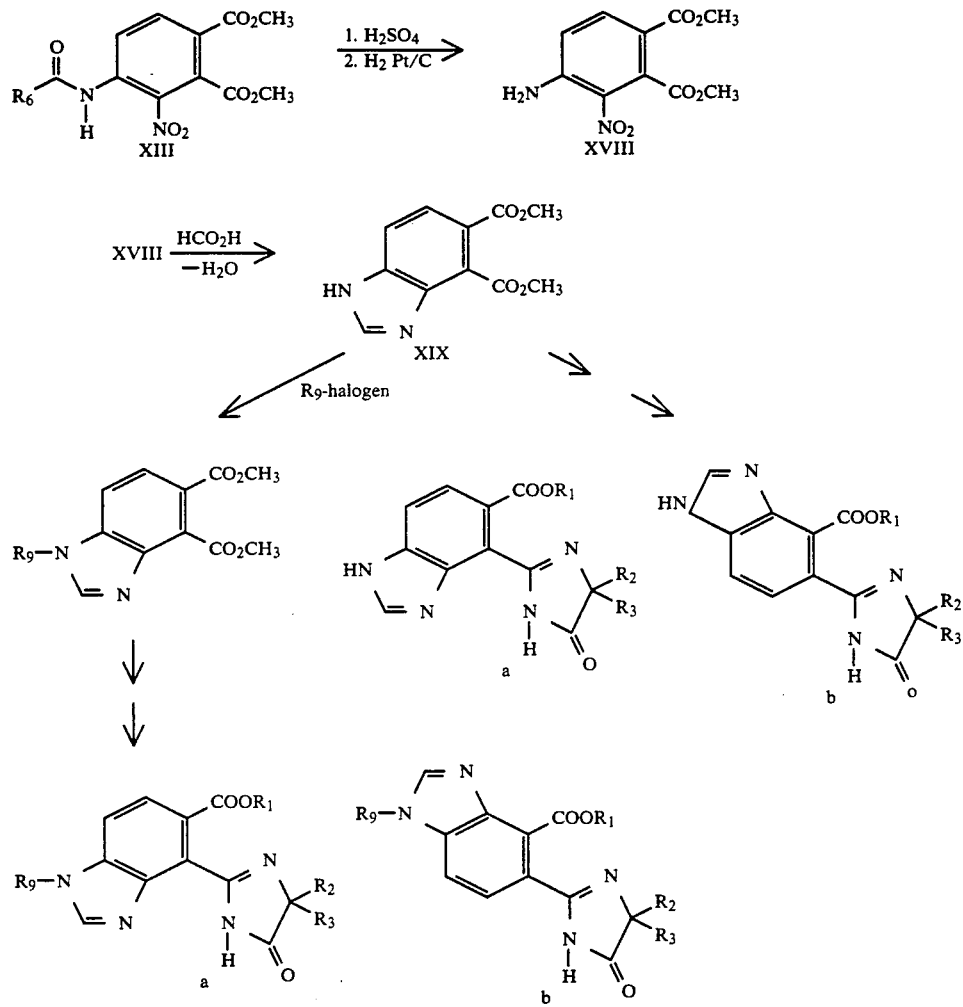

imidazole diesters of formula XIV and XIX. The reaction scheme is illustrated in flow diagram XIII.

FLOW DIAGRAM XIII

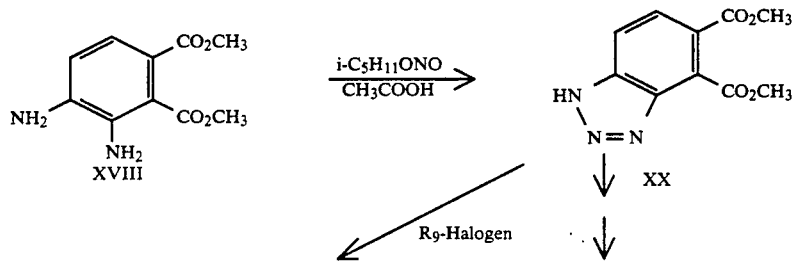

-continued
FLOW DIAGRAM XIII

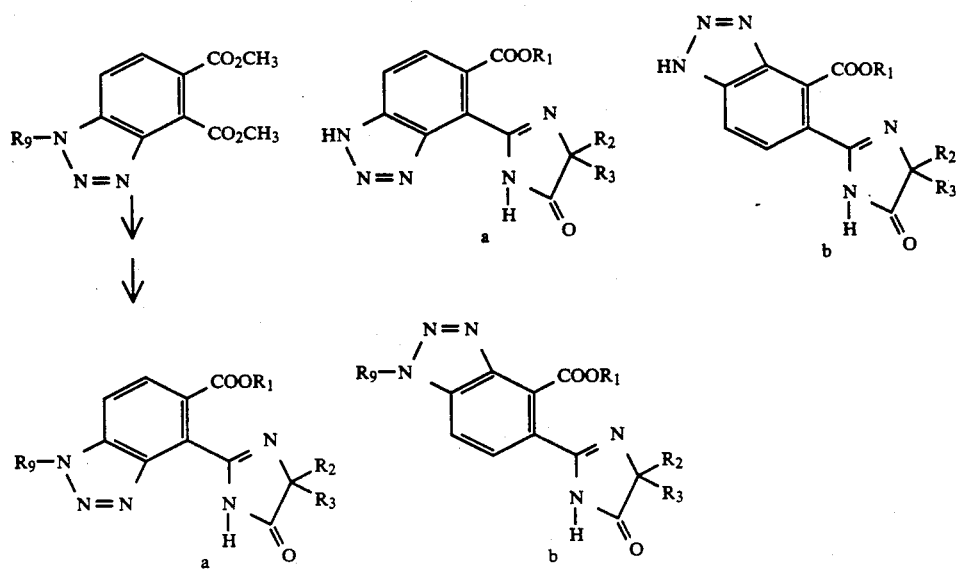

Of course, all of the compounds hereinabove described having structure a or b wherein $R_1$ and B are hydrogen can be converted to the corresponding imidazolinyl indoloheterocyclic diones having structure e and f by repeating the procedure illustrated in flow diagram VI. The corresponding imidazolinyl indoloheterocyclic diones having structure c and d can be prepared by reacting said imidazolinyl benzoheterocycles with an acid anhydride, optionally in the presence of a solvent, as shown in flow diagram XIV.

Compounds having structure a or b wherein $R_1$ is other than hydrogen or a cation, $R_9$ is other than hydrogen and B is $COR_4$ or $SO_2R_5$ may be prepared by reacting compounds having structure a or b wherein $R_1$ is other than hydrogen or a cation, $R_9$ is other than hydrogen and B is hydrogen with an acyl halide such as an acyl chloride or a sulfonyl halide such as a sulfonyl chloride to obtain the desired products wherein B is $COR_4$ or $SO_2R_5$. The reaction is shown in flow diagram XV.

FLOW DIAGRAM XIV

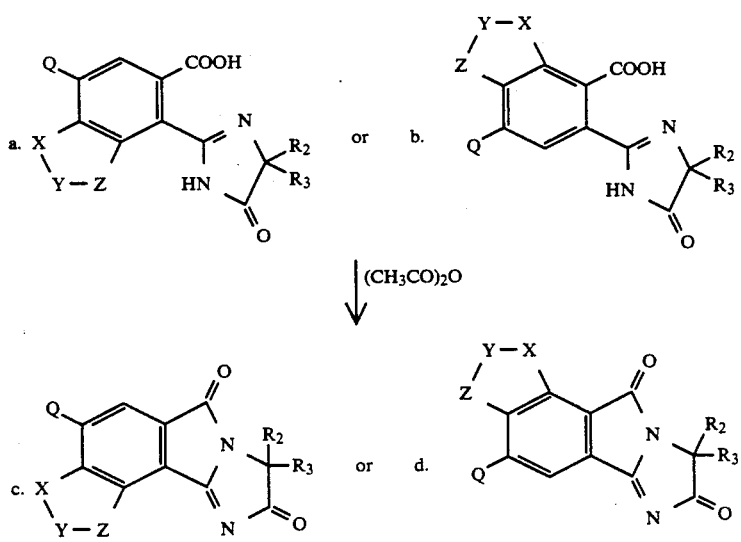

FLOW DIAGRAM XV

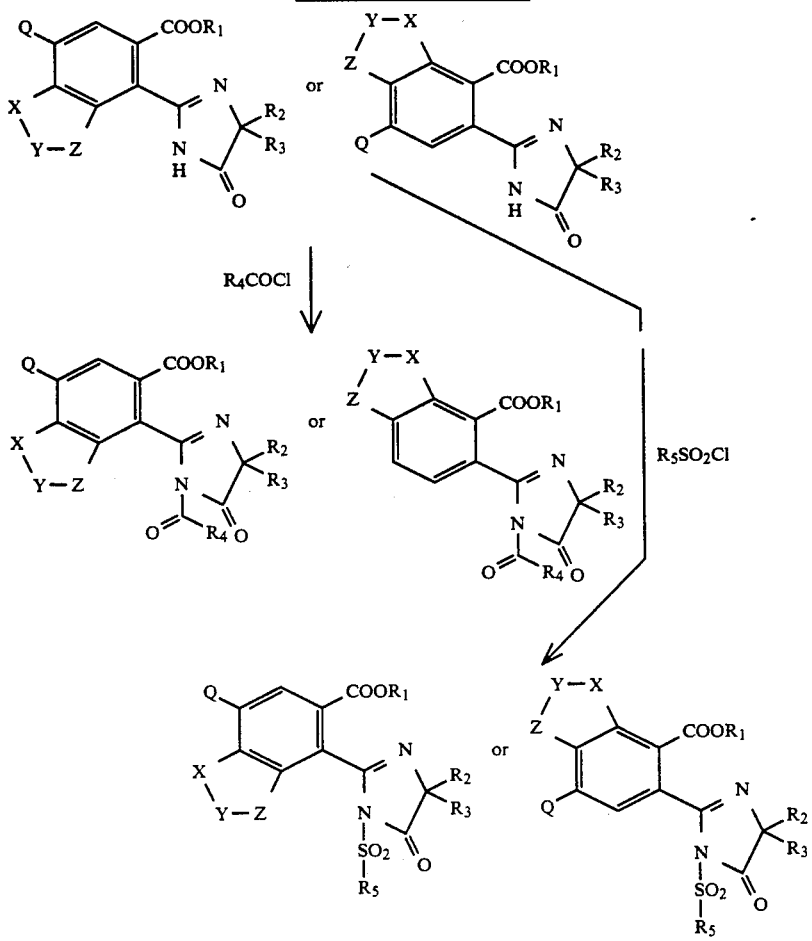

Alternatively, compounds having structure a or b wherein $R_1$ is other than hydrogen or a cation, $R_9$ is other than hydrogen and B is $COR_4$ may be prepared by reacting compounds having structure a or b wherein $R_1$ is other than hydrogen or a cation, $R_9$ is other than hydrogen and B is hydrogen with an acid anhydride of formula $(R_4CO)_2O$.

The imidazolinyl benzoheterocyclic compounds of the present invention are highly effective for controlling a variety of undesirable monocotyledenous plant species such as barnyardgrass, foxtail, purple, nutsedge, wild oats, quackgrass and the like and dicotyledenous plant species such as field bindweed, matricaria, morningglory, wild mustard, ragweed, velvetleaf and the like. Control of the above-said plant species can be achieved by applying the compounds of the invention to the foliage of said plants or to soil or water containing seeds or other propagating organs thereof at rates of about 0.016 to 4.0 kg/ha.

Surprisingly, it has been found that certain compounds of the invention are well tolerated by broadleaf crops such as soybeans and sugarbeets when said compounds are applied to the foliage of said crops or to soil containing the seeds or propagating organs thereof at rates of about 0.016 to 1.000 kg/ha.

Soybeans are an increasingly important worldwide source of high quality protein and are the most important edible legume produced today. Sugarbeets are a major source of sugar in North America, approximately one-third of the sugar consumed comes from sugarbeets. In Europe, sugarbeets are the primary source of refined sugar. By combining weed control with crop tolerance, the application of the compounds of the invention promotes improvement in field management, time of harvest and quantity and quality of harvest.

The imidazolinyl benzoheterocyclic compounds may be applied in the form of liquid sprays such as aqueous concentrates, emulsifiable concentrates and the like or as solid formulations such as wettable powders, dispersable granulars, granular formulations and the like.

When the herbicidally active compounds are water soluble, the may simply be dissolved in water and applied as an aqueous spray. Said compounds may also be formulated as emulsifiable concentrates and diluted with water just prior to spray application. A typical emulsifiable concentrate composition can be prepared by dissolving about 5% to 25% by weight of the active compound in about 65% to 90% by weight of N-methylpyrrolidone, isophorone, butyl cellosolve, methyl acetate or the like and dispersing therein about 5% to 10% by weight of a nonoionc surfactant such as an alkylphenoxy polyethoxy alcohol.

Wettable powder compositions can be prepared by grinding together about 20% to 45% by weight of a finely divided carrier such as kaolin, bentonite, diatomaceous earth, attapulgite or the like with about 40% to 80% by weight of the herbicidally active compound and about 2% to 5% by weight of a nonionic surfactant such as an alkyl phenoxy polyethoxy alcohol.

Typical granular products can be prepared by dissolving the active compound in a solvent such as methylene chloride, N-methylpyrrolidone or the like and spraying the resultant solution on a clay carrier such as attapulgite, or kaolin or the like in such a manner so as to produce about 3% to 20% by weight of the active compound and about 80% to 97% by weight of the carrier.

In order to facilitate a further understanding of the invention, the following examples are presented primarily for the purpose of illustrating certain more specific details thereof. The invention is not to be deemed limited thereby except as defined in the claims.

The term kg/ha designates kilograms per hectare. The terms NOE, $^1$HNMR and IR designate nuclear Overhauser effect, proton nuclear magnetic resonance and infrared, respectively. The term HPLC designates high pressure liquid chromatography. All parts are parts by weight, unless otherwise noted.

EXAMPLE 1

Preparation of Dimethyl 4-acetamido-5-nitrophthalate (I), and dimethyl 4-acetamido-3-nitrophthalate (II)

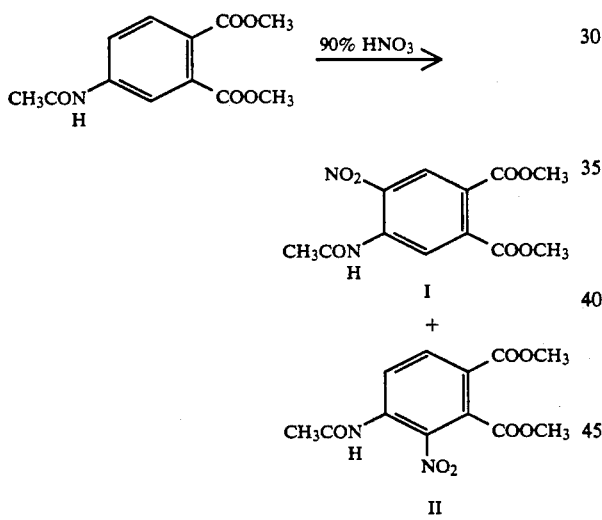

Dimethyl 4-acetamidophthalate (100.4 g, 0.400 mol) is added to fuming nitric acid (90%, 600 mL) at 0° C. to 5° C. When the addition is completed (0.5 hour), the mixture is stirred 2.5 hours at 0° C. to 10° C., combined with cold methylene chloride and shaken with crushed ice. The aqueous layer is separated and extracted further with methylene chloride. The combined organic layers are washed with ice water, sodium bicarbonate solution and cold water, dried (MgSO$_4$) and concentrated in vacuo to give a solid residue. The residue is recrystallized twice from methanol to afford the title product I as orange-brown needles, mp 119°–120° C. The original mother liquor is concentrated in vacuo, and the residue is recrystallized several times from carbon tetrachloride to afford the title compound II as light yellow needles, mp 124°–125° C. The yield of compound I is 38.9 g (32.9%), and the yield of compound II is 33.1 g (28.1%).

EXAMPLE 2

Preparation of Dimethyl 2-methyl-4,5-benzimidazoledicarboxylate

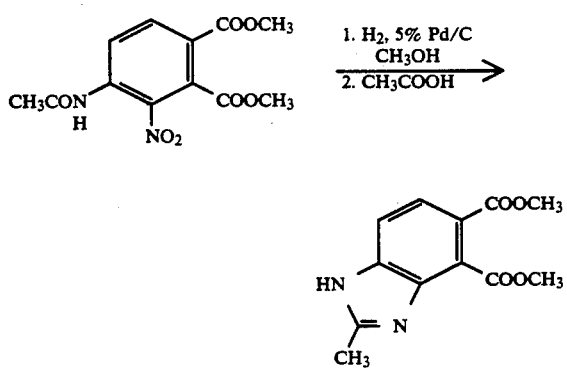

A mixture of dimethyl 4-acetamido-3-nitrophthalate (142.1 g, 0.480 mol) in methanol with 5% platinum on carbon catalyst is hydrogenated on a Parr hydrogenator at room temperature. The reaction mixtures is filtered through diatomaceous earth and concentrated in vacuo to afford a solid residue. This solid is dispersed in glacial acetic acid and toluene, and heated with stirring at reflux temperatures for 4 hours with azeotropic removal of water. The resultant hot reaction mixture is slowly added to a saturated sodium bicarbonate solution with vigorous stirring, filtered and the filter cake dried to give the title product as a white solid (71.6 g, 60.1%), mp 97°–103° C.

EXAMPLE 3

Preparation of 2-Methyl-4,5-benzimidazoledicarboxylic acid

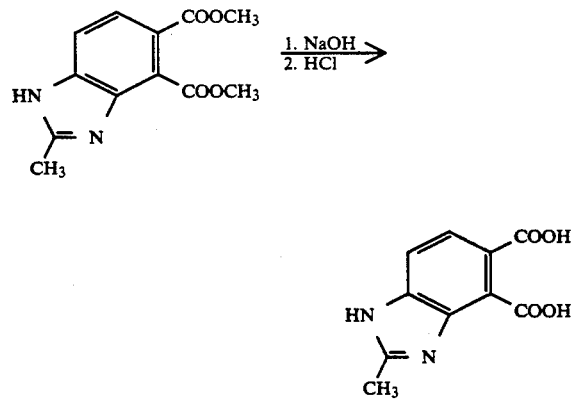

A mixture of dimethyl 2-methyl-4,5-benzimidazoledicarboxylate and 8 equivalents of 10N sodium hydroxide is stirred 4 hours at 70° C., cooled and acidified with hydrochloric acid to afford the title product as cream-colored crystals, mp 270° C. (dec).

EXAMPLE 4

Preparation of
4-(4-Isopropyl-4-methyl-5-oxo-2-imidazolin-2-yl)-2-methyl-4-benzimidazole carboxylic acid (I) and
5-(4-isopropyl-4-methyl-5-oxo-2-imidazolin-2-yl)-2-methyl-4-benzimidazolecarboxylic acid (II) 4:1 mixture

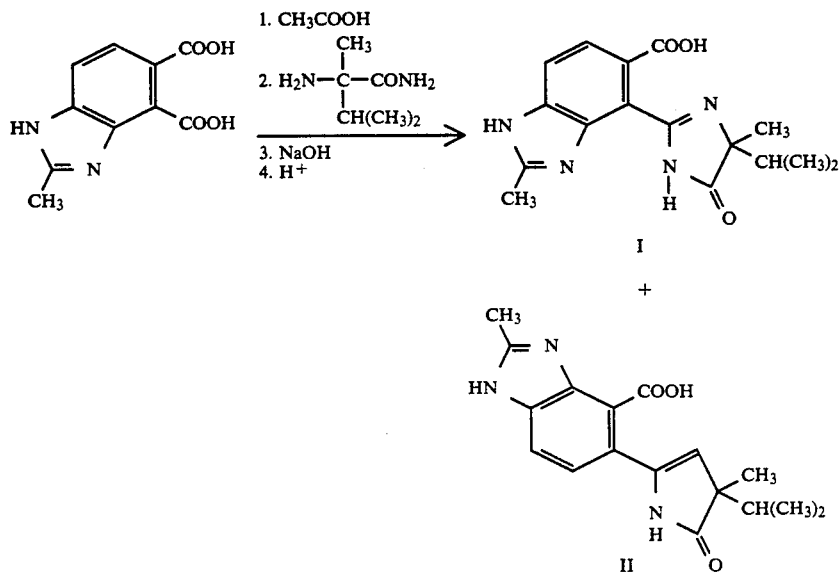

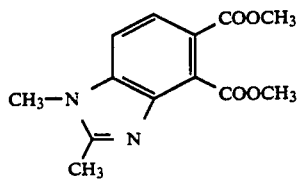

A mixture of 2-methyl-4,5-benzimidazoledicarboxylate (5.00 g, 22.7 mmol) and acetic anhydride is stirred for 6 hours at reflux temperature, cooled and concentrated in vacuo to give a residue. The residue is taken up in acetonitrile and treated with a-methylvaliramide (5.90 g, 45.3 mmol). The resultant mixture is stirred for 15 hours at reflux temperature, cooled and allowed to stand overnight. The solidified reaction mixture is taken up in 5N sodium hydroxide, heated at reflux temperatures for 10 hours with stirring, and filtered hot. The filtrate is acidified to pH 4 with concentrated HCl to afford a brown solid precipitate which is removed by filtration. The brown solid is heated in methanol, filtered hot, and the filtrate is concentrated in vacuo to afford the title product as a 4:1 ratio of I:II, respectively, as a yellow powder (0.93 g, 13.0%), mp 256° C. (dec).

EXAMPLE 5

Preparation of Dimethyl
1,2-dimethyl-4,5-benzimidazoledicarboxylate

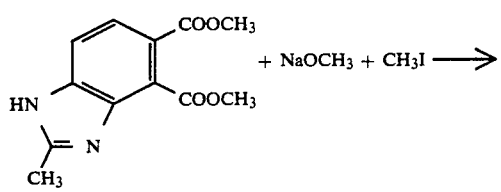

Sodium methoxide (1.98 g, 36.6 mmol) is added to a solution of dimethyl 2-methyl-4,5-benzimidazoledicarboxylate (7.44 g, 33.3 mmol) in methanol and tetrahydrofuran. After 5 minutes, iodomethane (2.18 mL, 35.0 mmol) is added and the mixture is stirred for 24 hours at room temperature. Additional sodium methoxide (1.80 g, 33.3 mmol) and iodomethane (2.07 mL, 33.3 mmol) are added and stirring is continued for another 15 hours. The reaction mixture is concentrated in vacuo to give a residue which is dispersed in dilute hydrochloric acid, and treated with sodium bicarbonate to pH 8 and extracted with chloroform. The combined organic extracts are dried (MgSO₄) and concentrated in vacuo to give a residue which is recrystallized from ethyl acetate to afford the title product as an orange solid, mp 205°-208° C.

EXAMPLE 6

Preparation of
1,2-Dimethyl-4,5-benzimidazoledicarboxylic acid

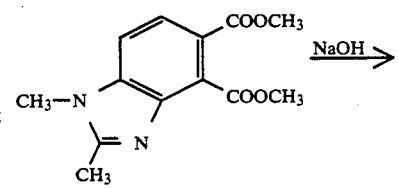

-continued

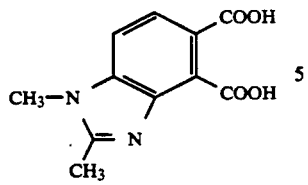

A mixture of dimethyl 1,2-dimethyl-4,5-benzimidazoledicarboxylate (1.70 g, 6.49 mmol) and 2N sodium hydroxide (25 mL, 12.5 mmol) is stirred for 5 hours at 100° C. The mixture is cooled, acidified to pH 4 with hydrochloric acid and filtered to afford the title product as a white powder (1.32 g, 86.8%), mp 305°-308° C. (dec).

EXAMPLE 7

Preparation of
1,2-Dimethyl-4,5-benzimidazoledicarboxylic anhydride

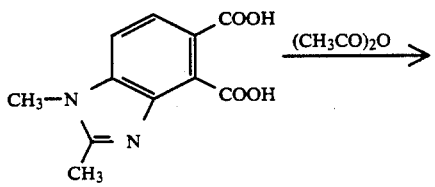

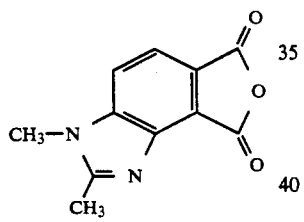

A mixture of 1,2-dimethyl-4,5-benzimidazoledicarboxylic acid (1.00 g, 4.27 mmol) and acetic anhydride (10 mL) is stirred 4 hours at reflux temperature, allowed to stand overnight at room temperature and filtered to afford the title product as yellow crystals (0.830 g, 89.8%), mp 295° C. (dec).

EXAMPLE 8

Preparation of
4-[(1-Carbamoyl-1,2-dimethylpropyl)-carbamoyl]-1,2-dimethyl-6-benzimidazolecarboxylic acid (I)
5-[(1-carbamoyl-1,2-dimethylpropyl)carbamoyl]-1,2-dimethyl-4-benzimidazolecarboxylic acid (II), 4:1 mixture

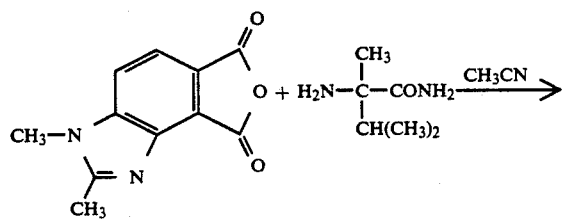

-continued

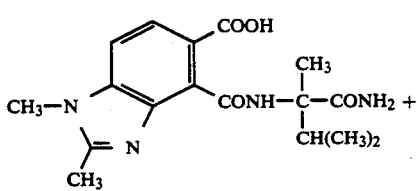

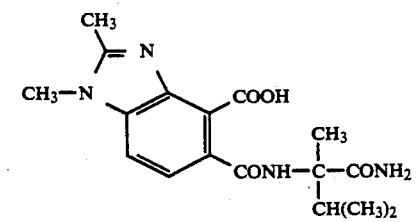

A mixture of 1,2-dimethyl-4,5-benzimidazoledicarboxylic anhydride (0.830 g, 3.85 mmol), a-methylvaliramide (0.550 g, 4.22 mmol) and acetonitrile is stirred for 4 hours at reflux temperature, cooled overnight and filtered to afford the title product as a white solid (1.24 g, 93.2%), mp 246°-248° C., identified by $^1$HNMR as a 4:1 mixture of compound I and compound II, respectively.

EXAMPLE 9

Preparation of
4-(4-Isopropyl-4-methyl-5-oxo-2-imidazolin-2-yl)-1,2-dimethyl-5 benzimidazolecarboxylic acid

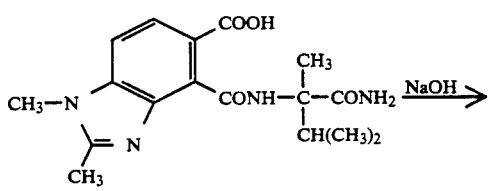

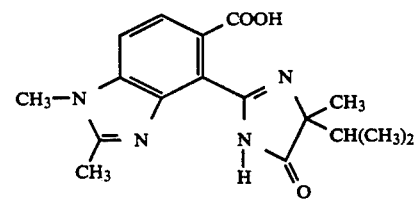

A solution of 4-[(1-carbamoyl-1,2-dimethylpropyl)-carbamoyl]-1,2-dimethyl-6-benzimidazolecarboxylic acid (5.70 g, 16.5 mmol) and 10N sodium hydroxide (9.88 mL, 98.8 mmol) is stirred for 3 hours at reflux temperatures, cooled to 0° C. and acidified to pH 4 with hydrochloric acid and filtered. The filter cake is dried to give the title product as a white solid (4.11 g, 75.8%), mp 280°-285° C. (dec).

EXAMPLE 10

Preparation of 9-Isopropyl-2,3,9-trimethylimidazo[1',2':1,2]pyrrolo[3,4-e]benzimidazole-6,8(3H,9H)-dione

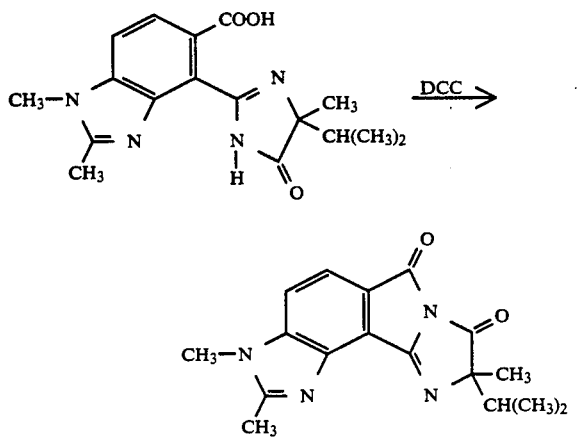

A mixture of 4-(4-isopropyl-4-methyl-5-oxo-2-imidazolin-2-yl)-1,2-dimethyl-5-benzimidazolecarboxylic acid (0.942 g, 2.87 mmol), dicyclohexylcarbodiimide (0.590 g, 2.87 mmol) and tetrahydrofuran is stirred for 3 hours at reflux temperature, cooled and concentrated in vacuo. The residue is chromatographed (silica gel, ethyl acetate eluent) to afford the title product as a white powder (0.210 g, 23.6%), mp 258°–263° C.

EXAMPLE 11

Preparation of Methyl 4-(4-isopropyl-4-methyl-5-oxo-2-imidazolin-2-yl)-1,2-dimethyl-5-benzimidazolecarboxylate

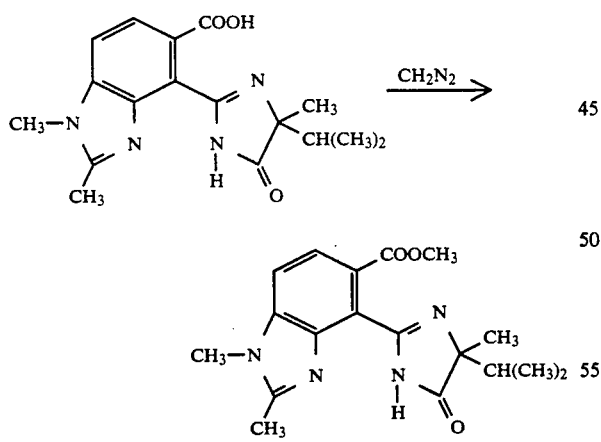

A solution of diazomethane in ether is added dropwise to a solution of the 4-(4-isopropyl-4-methyl-5-oxo-2-imidazolin-2-yl)-1,2-dimethyl-5-benzimidazolecarboxylic acid (2.50 g, 7.61 mmol) in methanol until the yellow color persists. The reaction mixture is neutralized with acetic acid and concentrated in vacuo. Preparative HPLC (silica gel, ethyl acetate eluent) affords the title product as off-white crystals (0.750 g, 28.9%), mp 240°–242° C.

EXAMPLE 12

Preparation of Dimethyl 1-benzyl-2-methyl-4,5-benzimidazoledicarboxylate

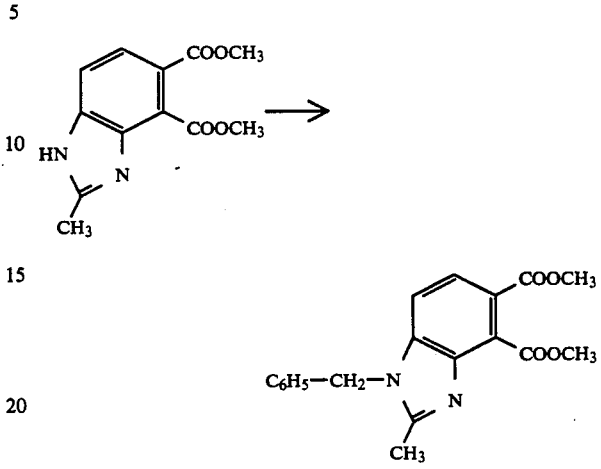

Sodium hydride (0.750 g, 80% oil dispersion, 25.0 mmol) is added, in portions, to a solution of dimethyl 2-methyl-4,5-benzimidazoledicarboxylate (6.07 g, 24.6 mmol) in dry dimethylformamide at 0° C. with stirring. After evolution of hydrogen ceases, benzyl bromide (2.93 mL, 24.6 mmol) is added to the reaction mixture and stirring is continued for 16 hours. The reaction mixture is concentrated in vacuo and the resultant residue is dispersed in methylene chloride and water. The phases are separated and the aqueous phase is extracted with methylene chloride. The organic phases are combined, dried and concentrated in vacuo to afford a solid residue. Recrystallization of the solid from ethyl acetate affords the title product as an off-white powder (3.81 g, 45.0%), mp 192°–195° C.

EXAMPLE 13

Preparation of 1-Benzyl-2-methyl-4,5-benzimidazoledicarboxylic acid

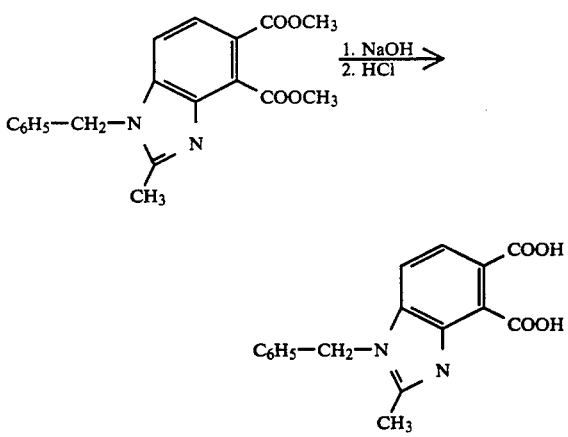

A mixture of dimethyl 1-benzyl-2-methyl-4,5-benzimidazoledicarboxylate (5.50 g, 16.2 mmol), methanol, 10N sodium hydroxide (13 mL, 130 mmol) and Water is stirred for 4 hours at 70° C., cooled, acidified to pH 4 with hydrochloric acid and filtered to afford the title product as an off-white solid (4.94 g, 98.4%), mp 224°–226° C.

EXAMPLE 14

Preparation of
1-Benzyl-2-methyl-4,5-benzimidazoledicarboxylic anhydride

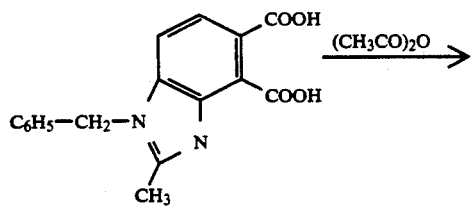

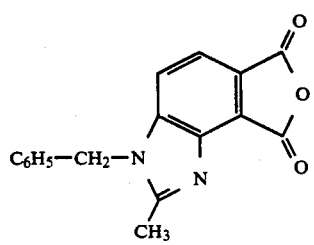

A mixture of the 1-benzyl-2-methyl-4,5-benzimidazoledicarboxylic acid (4.40 g, 14.2 mmol) and acetic anhydride is stirred for 5 hours at reflux temperature, cooled to 0° C. and filtered to give the title product as a pale yellow solid (3.78 g, 91.1%), identified by $^1$HNMR spectrography.

EXAMPLE 15

Preparation of
1-Benzyl-4-[(1-carbamoyl-1,2-dimethylpropyl)carbamoyl]-2-methyl-5-benzimidazolecarboxylic acid (I)
and
1-benzyl-5[(1-carbamoyl-1,2-dimethylpropyl-carbamoyl]-2-methyl-4-benzimidazolecarboxylic acid (II), 4:1 mixture

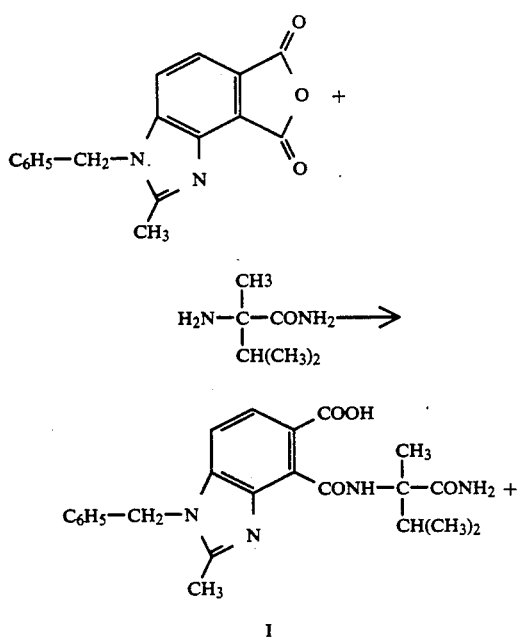

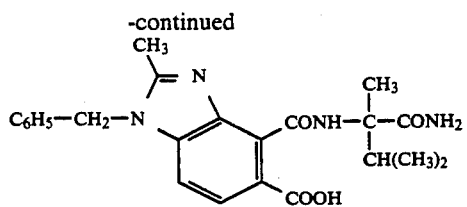

A mixture of 1-benzyl-2-methyl 4,5-benzimidazoledicarboxylic anhydride (3.70 g, 12.7 mmol), a-methylvaliramide (1.70 g, 13.0 mmol) and acetonitrile is stirred for 6 hours at reflux temperature, cooled to 0° C. and filtered to afford the title product, a 4:1 mixture of compound I and compound II, respectively, as an off-white powder (4.08 g, 76.1%), mp 194°-196° C. Product ratio is determined by $^1$HNMR spectral analysis.

EXAMPLE 16

Preparation of
1-Benzyl-4-(4-isopropyl-4-methyl-5-oxo-2-imidazolin-2-yl)-2-methyl-5-benzimidazolecarboxylic acid

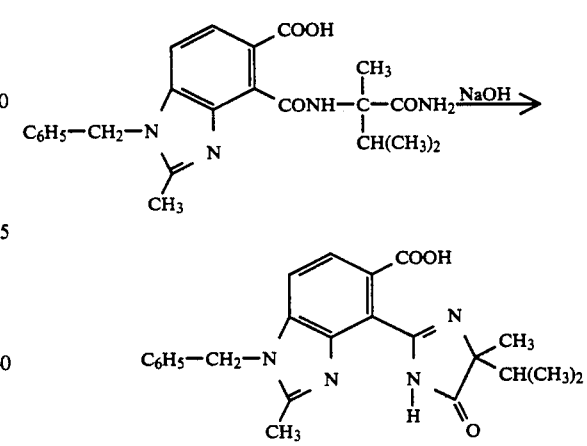

A mixture of 1-benzyl-4-[(1-carbamoyl-1,2-dimethylpropyl)carbamoyl]-2-methyl 5-benzimidazolecarboxylic acid (3.58 g, 8.47 mmol), 10N sodium hydroxide (5.08 mL, 50.8 mmol) and water is stirred for 4 hours at reflux temperature, cooled, acidified to pH 4 with hydrochloric acid and filtered. The filter cake is recrystallized from acetonitrile to give the title product as an off-white powder (1.06 g, 31.0%), mp 198°-208° C. (dec).

EXAMPLE 17

Preparation of Methyl
1-benzyl-4-(4-isopropyl-4-methyl-5-oxo-2-imidazolin-2-yl)-2-methyl-5-benzimidazolecarboxylate -continued

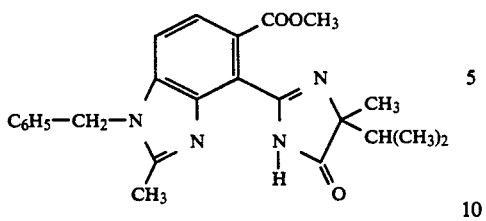

A solution of diazomethane in ether is added to a suspension of 1-benzyl-4-(4-isopropyl-4-methyl-5-oxo-2-imidazolin-2-yl)-2-methyl-5-benzimidazolecarboxylic acid (1.15 g, 2.84 mmol) in methanol until the yellow color persists The reaction is stirred for 5 minutes, quenched with 2 drops of acetic acid and concentrated in vacuo. The resultant residue is purified by HPLC (silica gel, ethyl acetate eluent) to give the title product as a white powder (0.480 g, 40.3%), mp 194°–196° C.

EXAMPLE 18

Preparation of Dimethyl 1-ethyl-2-methyl-4,5-benzimidazoledicarboxylate

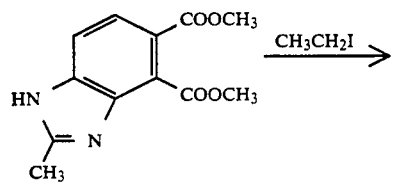

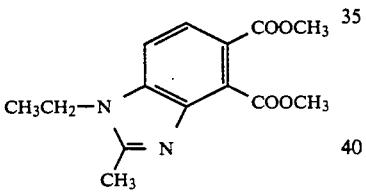

Sodium hydride (1.38 g, 46.0 mmol, 80% oil dispersion) is added in portions to a solution of dimethyl 1-benzyl-2-methyl-4,5-benzimidazoledicarboxylate (10.9 g, 43.8 mmol) in dry dimethylformamide at 0° C. After evolution of hydrogen ceases, ethyl iodide (3.68 mL, 46.1 mmol) is added. The reaction mixture is stirred at room temperature overnight, treated with ethyl acetate, and filtered. The filtrate is concentrated in vacuo; the resultant residue is recrystallized from 50% ethyl acetate:hexanes to yield the title product as a light yellow powder (3.84 g, 31.7%), mp 126.5°–128° C.

EXAMPLE 19

Preparation of 1-Ethyl-2-methyl-4,5-benzimidazoledicarboxylic acid

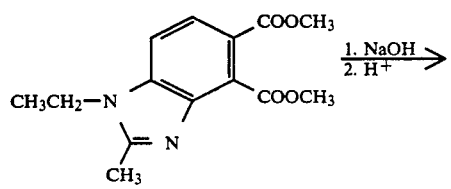

-continued

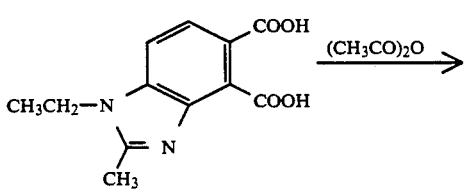

A mixture of dimethyl 1-ethyl-2-methyl-4,5-benzimidazoledicarboxylate (5.30 g, 19.2 mmol), methanol and 5N sodium hydroxide (30 mL, 150 mmol) is stirred for 4 hours at 100° C., cooled, acidified with hydrochloric acid and filtered to give the title product as a lemon yellow powder (4.07 g, 85.5%), identified by ¹HNMR spectral analysis.

EXAMPLE 20

Preparation of 1-Ethyl 2-methyl-4,5-benzimidazoledicarboxylic anhydride

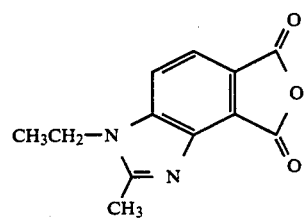

A mixture of 1-ethyl-2-methyl-4,5-benzimidazoledicarboxylic acid (4.00 g, 16.1 mmol) and acetic anhydride (50 mL) is stirred for 5 hours at reflux temperature, cooled and filtered. The filter cake is washed with ether and dried to give the title product as gold platelets (3.37 g, 90.8%), identified by ¹HNMR spectral analysis.

EXAMPLE 21

Preparation of 4-[(1-Carbamoyl-1,2 dimethylpropyl)-carbamoyl]-1-ethyl-2-methyl-5-benzimidazolecarboxylic acid (I) and 5-[(1-carbamoyl-1,2-dimethylpropyl)-carbamoyl]-1-ethyl-2-methyl-4-benzimidazocarboxylic acid (II), 4:1 mixture

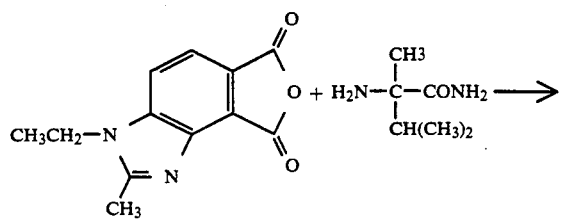

-continued

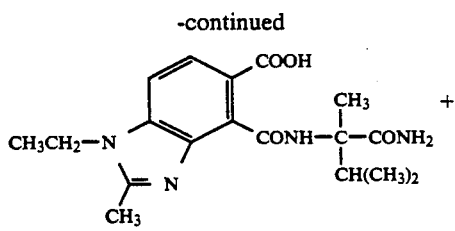

I

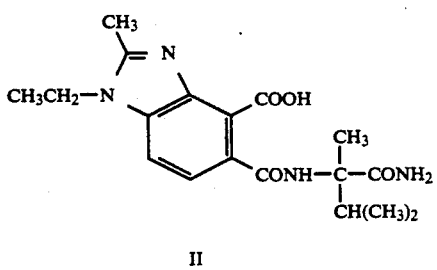

II

A mixture of 1-ethyl-2-methyl-4,5-benzimidazoledicarboxylic anhydride (3.30 g, 14.3 mmol), a-methylvaliramide (1.90 g, 14.5 mmol) and acetonitrile is stirred for 2 hours at reflux temperature, overnight at room temperature and 6 hours at reflux temperature. The mixture is cooled, concentrated in vacuo to 50% of its initial volume and filtered to give the title product as a 4:1 mixture of compound I and compound II, as a light yellow powder (4.59 g, 88.8%), mp 240°–243° C.

EXAMPLE 22

Preparation of 1-Ethyl-4-(4-isopropyl-4-methyl-5-oxo-2-imidazolin-2-yl)-2-methyl-5-benzimidazolecarboxylic acid

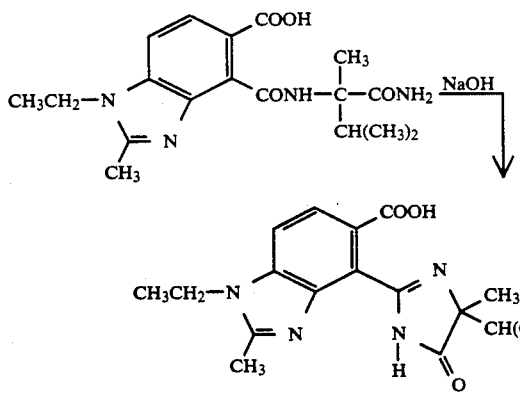

A mixture of 4-[(1-carbamoyl-1,2-dimethylpropyl)-carbamoyl]-1-ethyl-2-methyl-5-benzimidazolecarboxylic acid (4.09 g, 11.4 mmol), 10N sodium hydroxide (6.8 mL, 68.0 mmol) and water is stirred for 2 hours at reflux temperature, cooled, acidified to pH 4 with hydrochloric acid and filtered. The filter cake is recrystallized from acetonitrile to yield the title product as a white powder (1.10 g, 28.2%), mp 250°–256° C. (dec).

EXAMPLE 23

Preparation of Methyl 1-ethyl-4-(4-isopropyl-4-methyl-5-oxo-2-imidazolin-2-yl)-2-methyl-5-benzimidazolecarboxylate

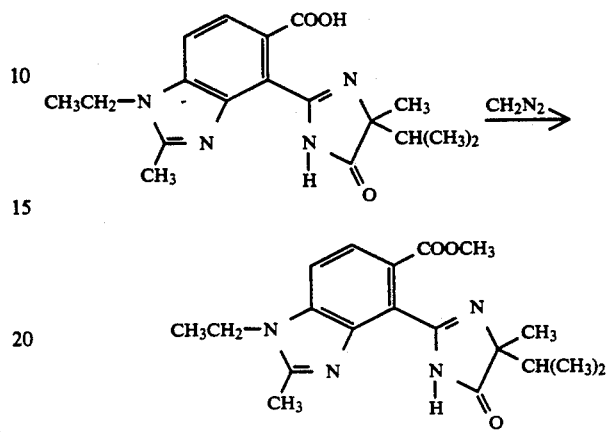

A solution of diazomethane in ether is added dropwise to a mixture of the starting carboxylic acid (2.10 g, 6.13 mmol) in methanol until the yellow color persists. After 5 minutes, the reaction mixture is quenched with acetic acid and concentrated in vacuo. The resultant residue is chromatographed (silica gel, HPLC, ethyl acetate eluent) to afford the title product as an off-white powder (1.03 g, 47.2%), mp 189°–191° C.

EXAMPLE 24

Preparation of Dimethyl 2-methyl-5,6-benzimidazoledicarboxylate

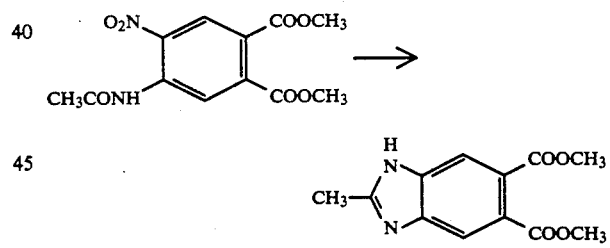

A mixture of dimethyl 4-acetamido-5-nitrophthalate, methanol and 5% platinum on carbon is hydrogenated in a Parr hydrogenator. The reaction mixture is filtered through diatomaceous earth and the filtrate is concentrated in vacuo. The thus-obtained crude diamine intermediate (48.09, 0.180 mol) is mixed with p-toluenesulfonic acid (51.4 g, 0.270 mol) and toluene (400 mL), and stirred for 2 hours at reflux temperatures with azeotropic removal of water, cooled and concentrated in vacuo. The resultant residue is recrystallized from methanol to afford the p-toluene sulfonate salt of the title product. The salt is dissolved in hot water, made basic with sodium bicarbonate and extracted with methylene chloride. The combined extracts are washed with brine, dried (MgSO$_4$) and concentrated in vacuo to give a red solid. Recrystallization of a portion of the red solid affords the title product as white crystals, mp 151°–152° C.

EXAMPLE 25

Preparation of Dimethyl
1,2-dimethyl-5,6-benzimidazoledicarboxylate

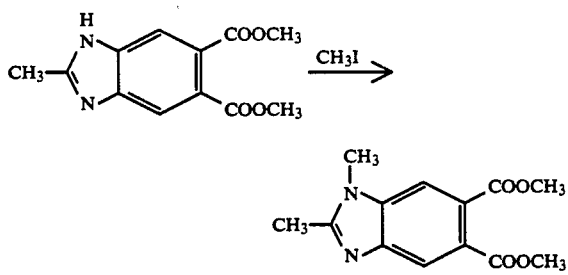

Sodium methoxide (1.96 g, 36.3 mmol) is added to a solution of dimethyl 2-methyl-5,6-benzimidazoledicarboxylate (8.50 g, 34.2 mmol) in methanol. The reaction mixture is stirred 0.5 hour at room temperature, treated with iodomethane (2.15 mL, 34.5 mmol) stirred overnight, acidified to pH 6 with acetic acid, treated with sodium bicarbonate to pH 8 and extracted with chloroform. The extracts are combined, dried (MgSO4) and concentrated in vacuo to yield the title product as a pink solid (6.25 g, 69.7%). A small portion is recrystallized from ethyl acetate to afford the title product as pink crystals, mp 147°–148° C.

EXAMPLE 26

Preparation of
1,2-Dimethyl-5,6-benzimidazoledicarboxylic acid

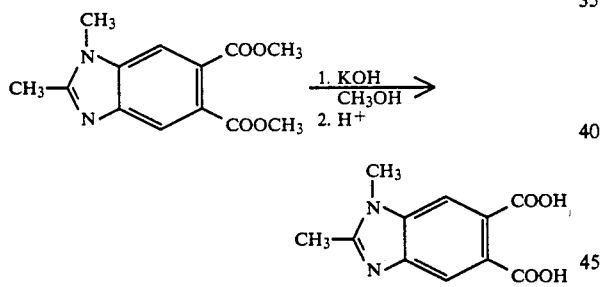

A mixture of dimethyl 1,2-dimethyl-5,6-benzimidazoledicarboxylate (2.80 g, 10.7 mmol), potassium hydroxide (1.49 g, 26.7 mmol), water and methanol is stirred at room temperature for 16 hours and then concentrated in vacuo. The resultant residue is taken up in a minimal amount of water, cooled, acidified to pH 3 with hydrochloric acid and filtered to give the title product as pink crystals (2.28 g, 91.2%), mp 308°–312° C.

EXAMPLE 27

Preparation of
1,2-Dimethyl-5,6-benzimidazoledicarboxylic anhydride

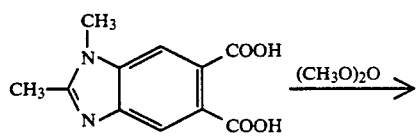

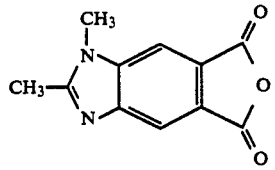

A mixture of the 1,2-dimethyl-5,6-benzimidazoledicarboxylic acid (1.25 g, 5.34 mmol) and acetic anhydride is stirred for 2 hours at reflux temperature, cooled to 5° and filtered. The filter cake is dried to give the title product as brown needles (1.04 g, 90.1%), mp 310°–315° C.

EXAMPLE 28

Preparation of
6-[(1-Carbamoyl-1,2-dimethyl-propyl)-carbamoyl]-1,2-dimethyl-5-benzimidazolecarboxylic acid (I) and
5-[(1-carbamoyl-1,2-dimethylpropyl)carbamoyl]-1,2-dimethyl-6-benzimidazole carboxylic acid (II)

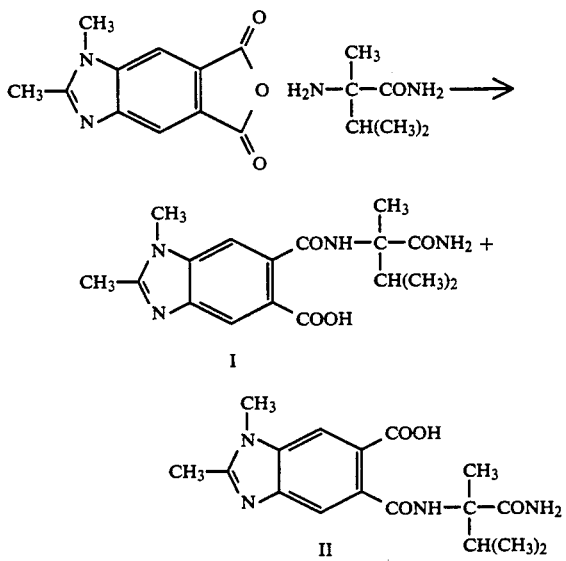

A mixture of 1,2-dimethyl-5,6-benzimidazoledicarboxylic anhydride (0.500 g, 2.31 mmol), a-methylvaliramide (0.300 g, 2.31 mmol) and acetonitrile is stirred for 3 hours at reflux temperature, cooled and filtered. Recrystallization of the filter cake from methanol affords the compound I as a white powder (0.230 g, 28.8%), mp 169°–171° C. The mother liquor is concentrated in vacuo to a yellow solid, which is recrystallized from methanol to afford title compound II as a white foam (0.240 g, 30.0%), mp 145°–150° C.

EXAMPLE 29

Preparation of
6-(4-Isopropyl-4-methyl-5-oxo-2-imidazolin-2-yl)-1,2-dimethyl-5-benzimidazolecarboxylic acid
dihydrochloride

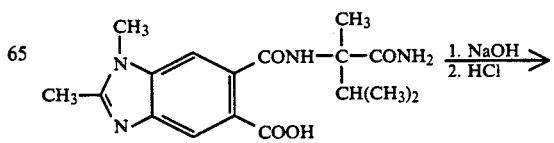

-continued

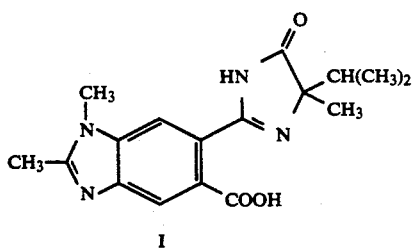

A mixture of 6-[(1-carbamoyl-1,2-dimethylpropyl)-carbamoyl]-1,2-dimethyl-5-benzimidazolecarboxylic acid (0.330 g, 0.910 mmol) and 2M sodium hydroxide (3.0 mL, 6.0 mmol) is stirred for 2.5 hours at reflux temperature, cooled, acidified to pH 3 with hydrochloric acid and filtered. The filter cake is recrystallized from ethanol to afford the title product as a white solid (0.120 g, 31.5%), mp 256°–258° C.

EXAMPLE 30

Preparation of Methyl 5-(4-isopropyl-4-methyl-5-oxo-2-imidazolin-2-yl)-1,2-dimethyl-benzimidazolecarboxylate

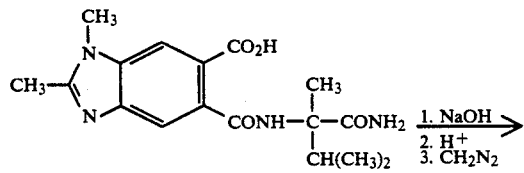

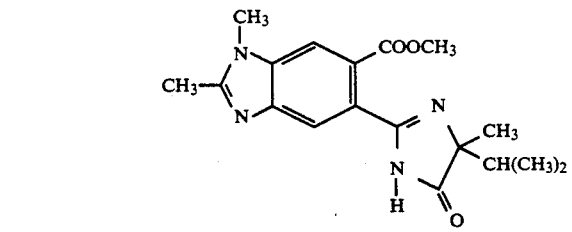

A mixture of the starting diamide (0.510 g, 1.47 mmol) and 2M sodium hydroxide (5.0 mL, 10.0 mmol) is stirred for 2.5 hours at reflux temperature, cooled, acidified to pH 3 with hydrochloric acid and filtered. The filtrate is concentrated in vacuo to give a white solid which is dissolved in methanol and treated with a solution of diazomethane in ether until the yellow color persists. The reaction mixture is quenched with acetic acid and concentrated in vacuo. The resultant residue is chromatographed (silica gel, 10% methanol:ethyl acetate eluent) to afford the title product as a white powder (0.140 g, 27.8%), mp 138°–140° C.

EXAMPLE 31

Preparation of Ethyl 4,5,6,7-tetrahydro-1,3-dimethyl-4-oxo-1H indazole-5-carboxylate

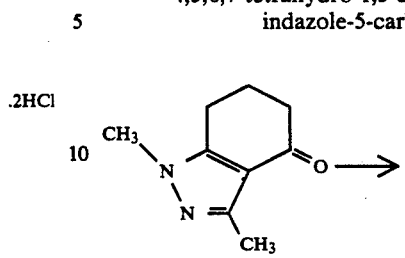

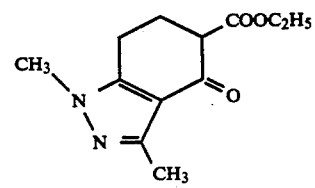

A suspension of sodium hydride (14.6 g, 0.365 mol, 60% oil dispersion) in dry benzene at 5° to 10° C. is treated with 1,5,6,7-tetrahydro-1,3-dimethyl-4H-indazole-4-one (30.0 g, 0.183 mol). The reaction mixture is treated dropwise with ethyl carbonate (45.0 mL, 0.365 mol) and ethanol (1.0 mL) with cooling, stirred for 11 hours at reflux temperature, cooled to room temperature and treated with acetic acid (24.1 g, 0.400 mol) and water. The phases are separated, the organic phase is set aside and the aqueous phase is extracted with ether. The organic phases are combined, washed with water, dried ($Na_2SO_4$) and concentrated in vacuo. The resultant residue is chased twice with toluene, recrystallized from (2:1) methylene chloride:heptane and a second time from 50% tetrahydrofuran:heptane to afford the title product (27.6 g, 63.9%), mp 76.5°–79° C.

EXAMPLE 32

Preparation of Ethyl 4-cyano-4,5,6,7-tetrahydro-1,3-dimethyl-4-(trimethylsilyloxy)-1H-indazole-5-carboxylate

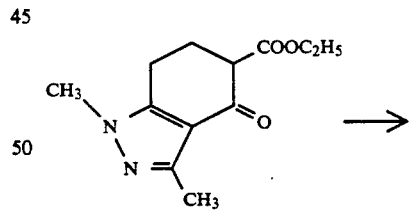

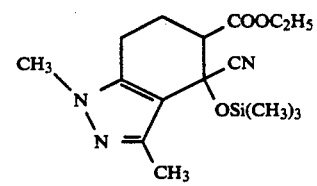

A solution of ethyl 4,5,6,7-tetrahydro-1,3-dimethyl-4-oxo-1H-indazole-5-carboxylate (41.0 g, 0.174 mol) in benzene is stirred at reflux temperatures with azeotropic removal of water for several hours, cooled to 65° C., treated with trimethylsilyl cyanide (58.0 mL, 0.440 mol) stirred for 15 minutes at 65° C., treated with zinc iodide (2.00 g, 0.00888 mol), stirred for 6 hours at 65° C., allowed to stand overnight at room temperature and concentrated in vacuo to afford the title product as an oil, identified by IR and mass spectroscopy.

EXAMPLE 33

Preparation of Ethyl 4-cyano-6,7-dihydro-1,3-dimethyl-1-H-indazole-5-carboxylate

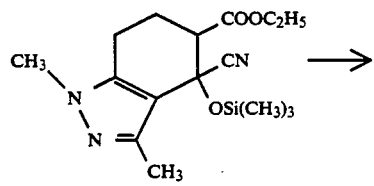

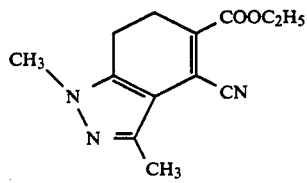

A solution of ethyl 4-cyano-4,5,6,7-tetrahydro-1,3-dimethyl-4-(trimethylsilyloxy)-1H-indazole-5-carboxylate (28.1 g, 0.119 mol) in pyridine is mixed with phosphorus oxychloride (43.0 mL, 0.461 mol), stirred for 5 hours at reflux temperature and concentrated in vacuo. The resultant black residue is diluted with ethyl acetate and water and treated with sodium bicarbonate to pH 6. The phases are separated, the organic phase is set aside, and the aqueous phase is extracted with ethyl acetate. The organic phases are combined, washed with aqueous sodium bicarbonate and water, dried (MgSO$_4$) and concentrated in vacuo to give a black residue. The residue is triturated under ethyl acetate to give the title product as a tan solid (15.5 g, 52.9%), identified by $^1$HNMR and IR spectroscopy.

EXAMPLE 34

Preparation of Ethyl 4-cyano-1,3-dimethyl-1H-indazole-5-carboxylate

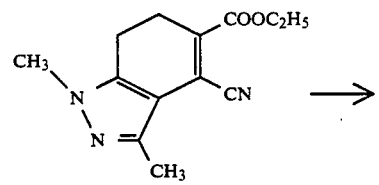

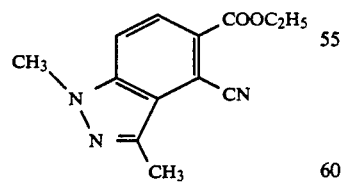

A mixture of ethyl 4-cyano-6,7-dihydro-1,3-dimethyl-1H-indazole-5-carboxylate (13.5 g, 55.0 mmol), o-chloranil (16.3 g, 66.0 mmol) and dry benzene is stirred for 1.5 hours at reflux temperature, cooled and filtered. The filtrate is concentrated in vacuo, filtered through two pads of neutral alumina and evaporated to dryness to afford a yellow solid. Recrystallization from ethyl acetate affords the title product (6.33 g, 47.2%), mp 170°–175.5° C.

EXAMPLE 35

Preparation of 1,3-Dimethyl-1H-indazole-4,5-dicarboxylic acid

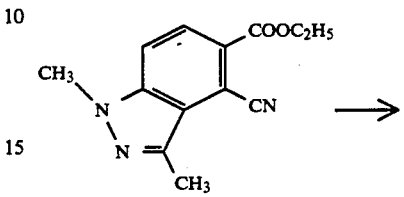

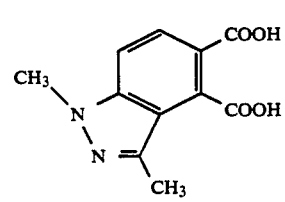

A mixture of ethyl 4-cyano-1,3-dimethyl-1H-indazole-5-carboxylate (7.03 g, 28.7 mmol), concentrated hydrobromic acid (35 mL) and acetic acid (35 mL) is stirred for 2 hours at reflux temperature, cooled, diluted with water (200 mL) and stirred for 2 hours. Filtration of the reaction mixture affords the title product as a pale blue solid (6.57 g, 97.8%), mp 228.5°–232.5° C.

EXAMPLE 36

Preparation of 1,3-Dimethyl-1H-indazole-4,5-dicarboxylic anhydride

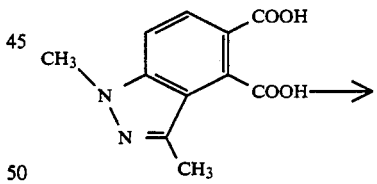

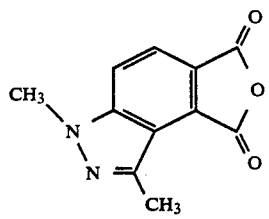

A mixture of 1,3-dimethyl-1H-indazole-4,5-dicarboxylic acid (6.30 g, 26.9 mmol) and acetic anhydride is stirred at reflux temperature for 3 hours, cooled to 5° C. and filtered. The filter cake is air-dried to give the title product as chartreuse needles (4.80 g, 82.5%), mp 214°–215.5° C.

EXAMPLE 37

Preparation of
4-[(1-Carbamoyl-1,2-dimethylpropyl)carbamoyl]1,3-dimethyl-1H-indazole-5-carboxylic acid

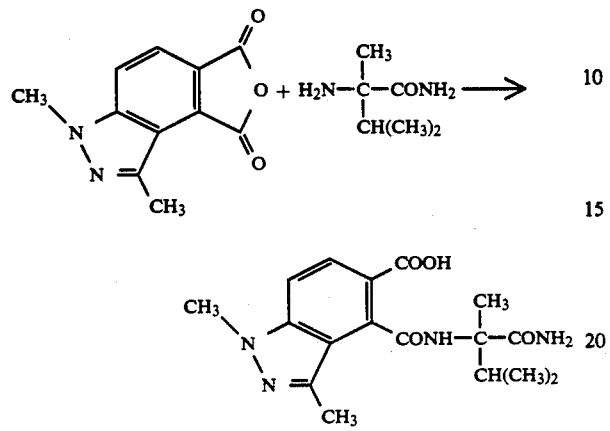

A mixture of 1,3-dimethyl-1H-indazole-4,5-dicarboxylic anhydride (1.60 g, 7.40 mmol), triethylamine (1.12 mL, 8.10 mmol), a-methylvarinamide (1.06 g, 8.14 mmol), dimethoxyethane and dimethylformamide is stirred for 16 hours at room temperature and concentrated in vacuo. The resultant residue is diluted with water and filtered to give the title product as a white solid. Acidification of the filtrate to pH 3 affords additional product, identified by $^1$HNMR, IR and mass spectra. The total yield is 2.00 g (78.1%).

EXAMPLE 38

Preparation of Methyl
4-(1-carbamoyl-1,2-dimethylpropyl)carbamoyl]-1,3-dimethyl-1H-indazole-5-carboxylate

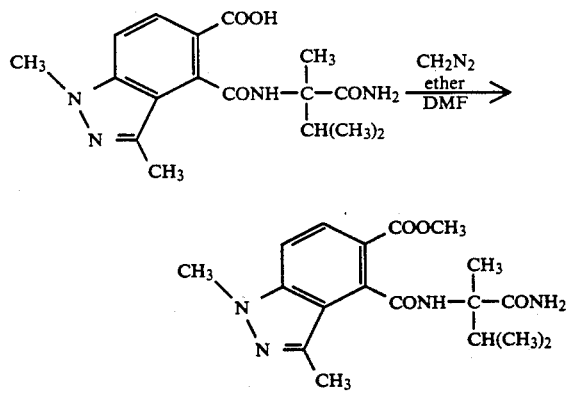

A solution of 4-[(1-Carbamoyl-1,2-dimethylpropyl)carbamoyl]1,3-dimethyl-1H-indazole-5-carboxylic acid (0.720 g, 2.07 mmol) in dry dimethylformamide is treated with sufficient ethereal diazomethane to give a permanent yellow color. The excess diazomethane is quenched with acetic acid, and the reaction mixture is concentrated in vacuo. The resultant residue is chased 2 times with xylene recrystallized from 50% aqueous methanol to give the title product as a white solid, mp 221°-222° C.

EXAMPLE 39

Preparation of Methyl
4-(4-isopropyl-4-methyl-5-oxo-2-imidazolin-2-yl)-1,3-dimethyl-1-H-indazole-5-carboxylate

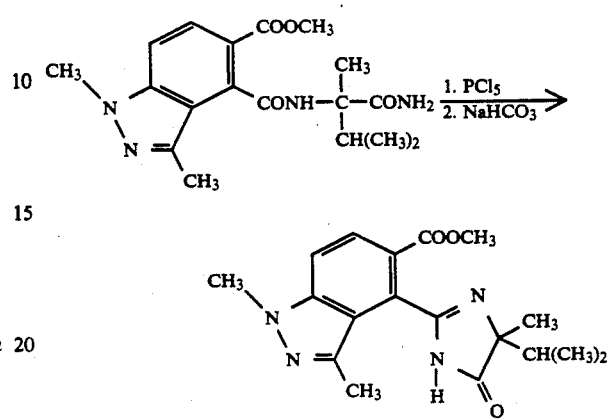

A mixture of methyl 4-[(1-carbamoyl-1,2-dimethylpropyl)carbamoyl]-1,3-dimethyl-1H-indazole-5-carboxylate (0.600 g, 1.67 mmol), phosphorus pentachloride (1.04 g, 5.00 mmol) and dry toluene (7.0 mL) is stirred for 3.5 hours at 90° C. cooled and filtered The filter cake is washed with toluene, slurried in water, treated with sodium bicarbonate (0.370 g, 4.40 mmol) to pH 8.5 and filtered to afford the title product as a white solid (0.490 g, 85.7%), mp 130°-150° C.

EXAMPLE 40

Preparation of
4-(4-Isopropyl-4-methyl-5-oxo-2-imidazolin-2-yl)-1,3-dimethyl-1H-indazole-5-carboxylic acid

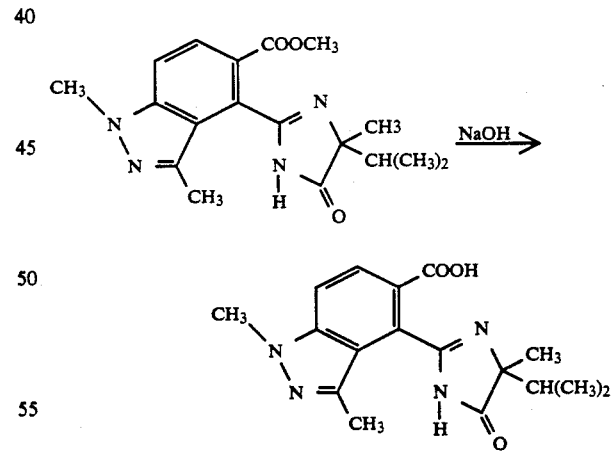

A mixture of methyl 4-(4-isopropyl-4-methyl-5-oxo-2-imidazolin-2-yl)-1,3-dimethyl-1H-indazole-5-carboxylate (0.310 g, 0.905 mmol), 2N sodium hydroxide (0.91 mL, 1.82 mmol) and tetrahydrofuran (11 mL) is stirred for 1.5 hours at 42°-52° C., cooled in an ice bath, acidified to pH 3-3.5 with 5N sulfuric acid and extracted with chloroform. The organic extract is dried (Na$_2$SO$_4$) and concentrated in vacuo to give a residue which is recrystallized from acetonitrile to afford the title product as a white solid (0.160 g, 53.2%), mp 156.5°-166° C.

EXAMPLE 41

Preparation of 1-Methylpyrrole-3-carboxaldehyde

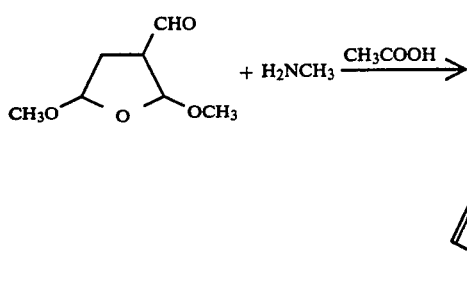

Monomethylamine (20 g, 0.64 mmol) is added, via a dry ice condenser, to a stirred solution of 2,5-dimethoxy-3-tetrahydrofurancarboxaldehyde (48.1 g, 0.300 mol) in glacial acetic acid (500 mL) at 10° C. The dry ice condenser is replaced with a water condenser and the reaction mixture is stirred for 2 hours at 110° C., cooled to room temperature and distilled at 25° to 30° C./4.0 torr to remove the acetic acid. The pot residue is diluted with ice water, washed with ether, cooled, treated with sodium hydroxide to pH 7, and extracted with methylene chloride. The organic extracts are combined, dried (MgSO4) and concentrated in vacuo to afford the title product as a red liquid (11.0 g, 33.6%), identified by $^1$HNMR spectroscopy.

EXAMPLE 42

Preparation of 1-Methyl-3-vinylpyrrole

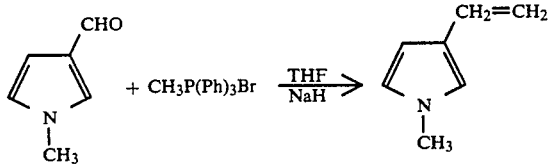

To a stirred slurry of sodium hydride (7.00 g, 0.174 mol, 60% oil dispersion) in dry tetrahydrofuran, under a nitrogen atmosphere, is added methyltriphenylphosphonium bromide (51.8 g, 0.145 mol). The mixture is stirred for 1 hour at reflux temperature, cooled to 45° C., and treated dropwise with a solution of 1-methylpyrrole-3-carboxaldehyde (15.8 g, 0.145 mol) in tetrahydrofuran. The resultant mixture is stirred for 6 days at room temperature and filtered through neutral alumina with petroleum ether as additional eluant. The filtrate is concentrated in vacuo to a yellow-white semi-solid residue which is diluted with petroleum ether and refiltered through neutral alumina. The colorless filtrate is concentrated in vacuo to afford the title product as a pale yellow oil (10.1 g, 65.2%), identified by $^1$HNMR spectroscopy.

EXAMPLE 43

Preparation of Hexahydro-a-isopropyl-a,1-dimethyl-6,8-dioxobenzo[2,1-b:3,4-c']dipyrrole-7(1-H)-acetonitrile

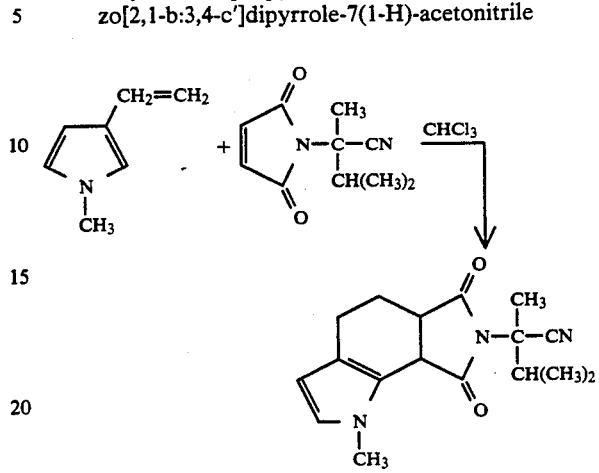

A mixture of 1-methyl-3-vinylpyrrole (9.50 g, 0.089 mol), a-isopropyl-a-methyl-2,5-dioxo-3-pyrroline-1-acetonitrile (17.0 g, 0.089 mol) and chloroform is stirred overnight at room temperature and concentrated in vacuo to an amber oil residue. The residue is flash chromatographed (silica gel, gradient elution: 50% hexanes: methylene chloride to ether) to afford the title product as an orange glass (13.0 g, 48.8%), identified by $^1$HNMR spectroscopy.

EXAMPLE 44

Preparation of 6,8-Dihydro-a-isopropyl-a,1 dimethyl-6,8-dioxobenzo[2,1-b 3,4-c']dipyrrole-7(1H)-acetonitrile

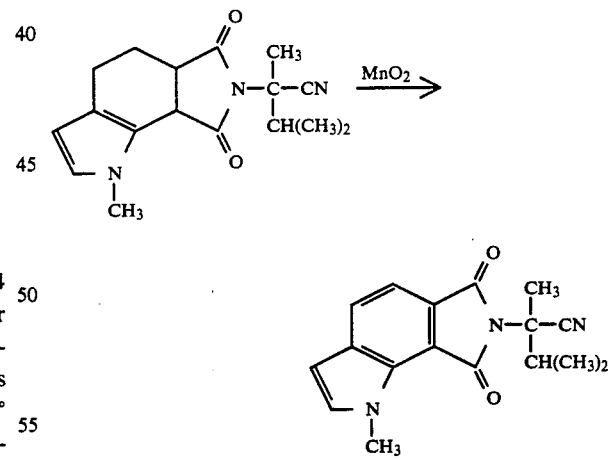

A mixture of hexahydro-2-isopropyl-a,1-dimethyl-6,8-dioxobenzo[2,1-b:3,4-c]dipyrrole-7(1H)-acetonitrile) (9.30 g, 30.0 mmol), manganese dioxide (7.00 g, 80.5 mmol) and chlorobenzene is stirred at reflux temperatures overnight, treated with additional manganese dioxide (3.50 g, 40.2 mmol) and heated for a further 16 hours at reflux temperature. A third portion of manganese dioxide (3.50 g, 40.2 mmol) is added and the reaction mixture is stirred for 3 days at reflux temperature, cooled to 25° C., and concentrated in vacuo to give a black residue. The residue is flash chromatographed (silica gel, 50% ether:hexane) to afford the title product as a yellow solid (4.30 g, 48.5%), mp 134°–138° C.

EXAMPLE 45

Preparation of 6,8-Dihydro-a-isopropyl-a,1-dimethyl-6,8-dioxobenzo[2,1-b:3,4-c']dipyrrole-7(1H)-acetamide

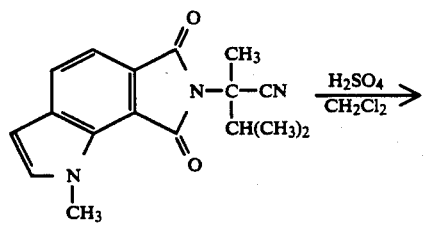

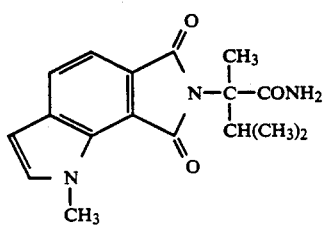

A solution of 6,8-dihydro-a-isopropyl-a,1-dimethyl-6,8-dioxobenzo[2,1-b:3,4-c']dipyrrole-7(1H)-acetonitrile (5.30 g, 18.0 mmol) in methylene chloride is added dropwise to concentrated sulfuric acid at 5°–10° C. with rapid stirring. The ice bath is removed and the reaction mixture is stirred overnight at ambient temperatures, poured over crushed ice, diluted with methylene chloride, treated with 50% sodium hydroxide solution with ice bath cooling to pH 3–4 and separated. The aqueous layer is extracted with methylene chloride. The combined organic layers are dried (MgSO4) and concentrated in vacuo to give an orange foam residue, which is recrystallized from methylene chloride to afford the title product as yellow crystals (1.30 g, 23.2%), mp 184°–189° C.

EXAMPLE 46

Preparation of 8-Isopropyl-1,8-dimethyl-1H-imidazo[1',2':1,2]pyrrolo[3,4-g]indole-6,9-dione and 8-isopropyl-1,8-dimethyl-1H-imidazo[2',1':5,1]pyrrolo-[3,4-g]-indole-7,10-dione (1:1 mixture)

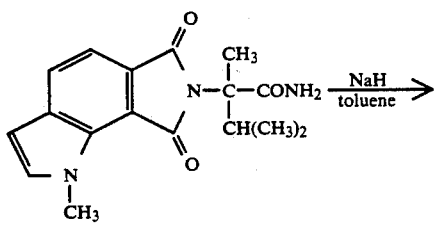

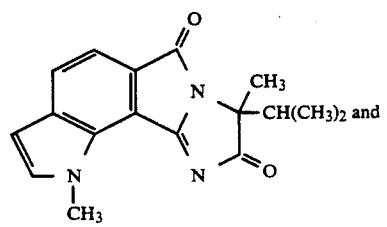

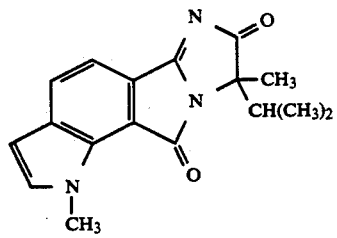

Sodium hydride (0.240 g, 6.00 mmol, 60% oil dispersion) is added portionwise to a mixture of 6,8-dihydro-a-isopropyl-a-1-dimethyl 6,8-dioxobenzo[2,1-b:3,4-c']dipyrrole-7(1H)-acetamide (0.900 g, 2.87 mmol) and dry toluene at reflux temperature. After 1 hour at reflux temperature, the mixture is cooled to room temperature and filtered through diatomaceous earth. The filtrate is concentrated in vacuo to afford the title product as an orange solid 0.900 g, 100%), identified by ¹HNMR spectral analysis.

EXAMPLE 47

Preparation of Methyl [7-(4-isopropyl-4-methyl-5-oxo-2-imidazolin-2-yl)-1-methyl]indole-6-carboxylate and methyl [6-(4-isopropyl-4-methyl-5-oxo-2-imidazolin-2-yl)-1-methyl]indole-7-carboxylate (1:1 mixture)

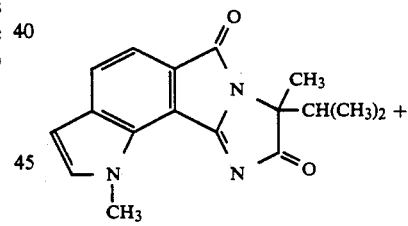

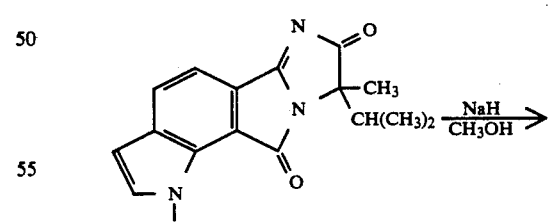

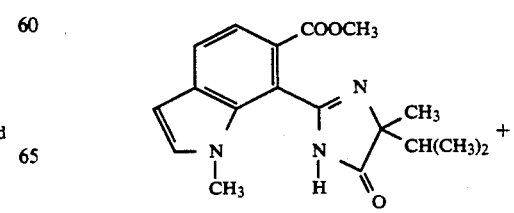

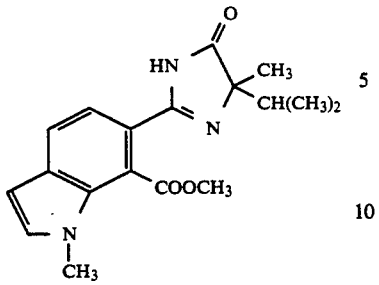

A catalytic amount of sodium hydride (60% oil dispersion) is added to a solution of a 1:1 mixture of 8-isopropyl-1,8-dimethyl-1H-imidazo[1'.2':1,2]pyrrolo[3,4-g]indole-6,9-dione and 8-isopropyl-1,8-dimethyl-1H-imidazo[2',1':5,1]pyrrolo[3,4-g]indole-7,10-dione (0.900 g, 3.00 mmol) in methanol at room temperature to pH 10. After 5 days, more sodium hydride is added to pH 10–11 and the reaction mixture is heated on a steam bath for 1 hour. After cooling to room temperature, acetic acid is added to pH 6 and the mixture is concentrated in vacuo. The residue is diluted with methylene chloride and water; the organic layer is dried (MgSO4) and concentrated in vacuo to afford the title product as a yellow foam (0.350 g, 35.7%). Identification is determined by $^1$HNMR spectral analysis.

EXAMPLE 48

Preparation of 7-(4-Isopropyl-4-methyl-5-oxo-2-imidazolin-2-yl)-1-methylindole-6-carboxylic acid and 6-(4-isopropyl-4-methyl-5-oxo-2-imidazolin-2-yl)-1-methylindole-7-carboxylic acid (1:1 mixture)

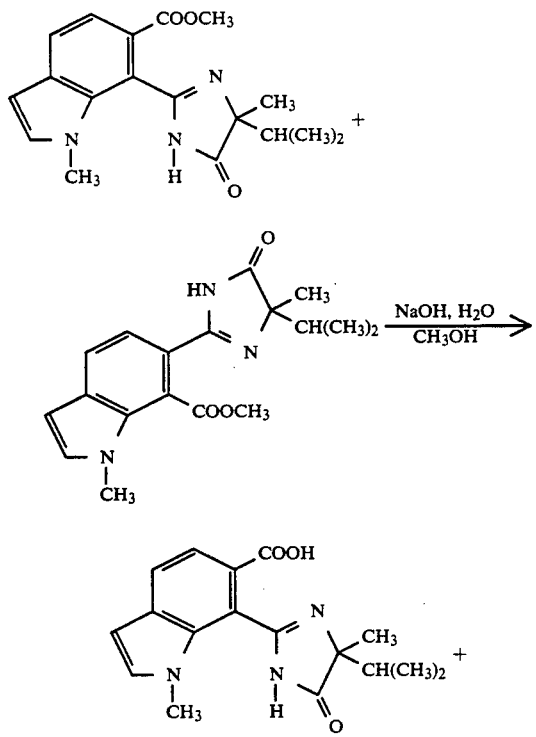

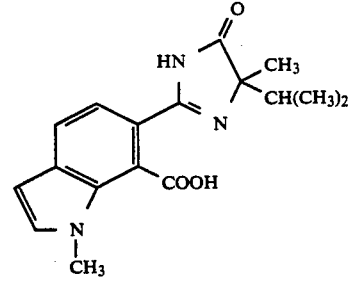

A 1:1 mixture of methyl [7-(4-isopropyl-4-methyl-5-oxo-2-imidazolin-2-yl)-1-methyl]indole-6-carboxylate and methyl [6-(4-isopropyl-4-methyl-5-oxo- 2-imidazolin-2-yl)-1-methyl]indole-7-carboxylate (0.350 g, 1.07 mmol), in methanol and 1.93N sodium hydroxide (0.60 mL, 1.16 mmol) is stirred overnight at room temperature. The reaction mixture is concentrated in vacuo and the residue is diluted with water, treated with concentrated hydrochloric acid to pH 3 and filtered to give the title product as a light yellow solid (0.140 g), mp 122°–140° C.

EXAMPLE 49

Preparation of 1-Methyl-2-vinylpyrrole

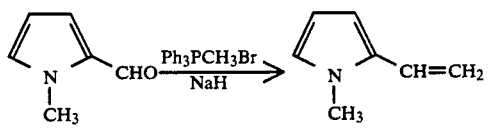

Methyltriphenylphosphonium bromide (35.7 g, 0.100 mol) is added to a slurry of sodium hydride (4.80 g, 0.120 mol, 60% oil dispersion) in dry tetrahydrofuran at 10° C. under a nitrogen atmosphere. The mixture is stirred at reflux temperature for 1 hour, cooled to 35° C., treated dropwise with a solution of 1-methylpyrrole-2-carboxaldehyde (10.9 g, 0.100 mol) in tetrahydrofuran, stirred for 3 days at ambient temperature, 2 hours at reflux and 16 hours at room temperature. The reaction mixture is filtered through neutral alumina with petroluem ether. The clear yellow filtrate is concentrated in vacuo to give a light yellow semi-solid residue which is taken up in petroleum ether and filtered through a cake of diatomaceous earth on neutral alumina. The resultant colorless filtrate is concentrated in vacuo to afford the title product as a clear, colorless oil (7.80 g, 72.5%), identified by $^1$HNMR spectroscopy.

EXAMPLE 50

Preparation of 3,3a,4,5,6,8b-Hexahydro-a-isopropyl-a,6-dimethyl-1,3-dioxobenzo[1,2-b:3,4-c']dipyrrole-2(1H)-acetonitrile

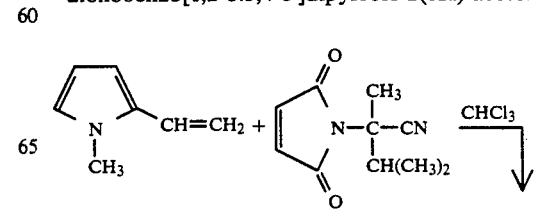

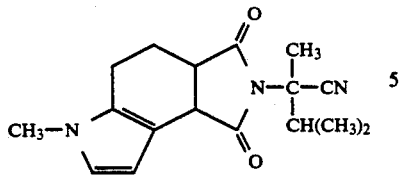

A mixture of 1-methyl-2-vinylpyrrole (3.90 g, 36.0 mmol), a-isopropyl-a-methyl-2,5-dioxo-3-pyrroline-1-acetonitrile (7.00 g, 36.0 mmol) and chloroform is stirred overnight at room temperature and concentrated in vacuo. The resultant residue is flash chromatographed (silica gel, 50% ether:hexanes eluent) to afford the title product as a clear yellow glass (63.5 g, 58.8%).

EXAMPLE 5

Preparation of
3,6-Dihydro-a-isopropyl-a,6-dimethyl-1,3-dioxobenzo[1,2-b:3,4-c']dipyrrole-2(1H)acetonitrile

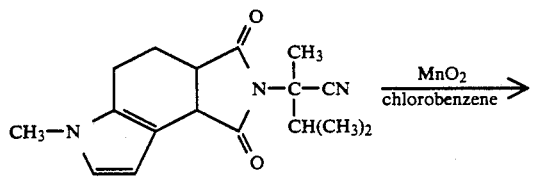

Activated manganese dioxide (27.0 g, 0.310 mol) is added to a solution of 3,3a,4,5,6,8b-hexahydro-a-isopropyl-a,6-dimethyl-1,3-dioxobenzo-[1,2-b:3,4-c']dipyrrole-2(1H)-acetonitrile (51.3 g, 0.167 mol) in chlorobenzene. The reaction mixture is stirred overnight at reflux temperature, cooled and filtered twice through diatomaceous earth with methylene chloride. The filtrate is concentrated in vacuo to a black oil which is flash chromatographed twice with methylene chloride then hexanes methylene chloride to afford a yellow solid (5.50 g, 11.6%). Recrystallization from hexanes:methylene chloride afforded the title product, mp 123°–128° C.

EXAMPLE 52

Preparation of
3,6-Dihydro-a-isopropyl-a,6-dimethyl-1,3-dioxobenzo[1,2-b:3,4-c']dipyrrole-2(1H)acetamide

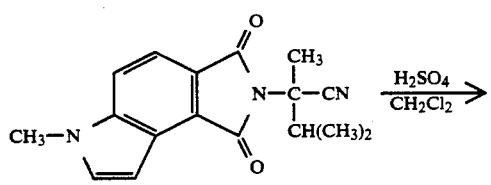

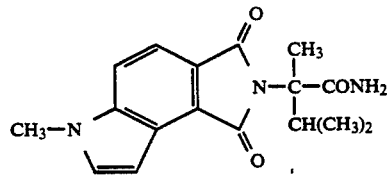

Concentrated sulfuric acid (5.50 mL) is added slowly to a solution of 3,6-dihydro-a-isopropyl-a,6-dimethyl-1,3-dioxobenzo[1,2-b:3,4-c']dipyrrole-2(1H)-acetonitrile (5.50 g, 19.0 mmol) in methylene chloride at 10° C. Crushed ice is added. The mixture is stirred for 24 hours at ambient temperature and poured onto crushed ice, treated with 6N sodium hydroxide to pH 2, and extracted with methylene chloride. The organic layer is separated, dried (MgSO4) and concentrated in vacuo to give an orange foamy residue. Flash chromatography (silica gel, ether then ethyl acetate eluents) affords the title product as a yellow foam (1.53 g, 25.7%), mp 159°–168° C.

EXAMPLE 53

Preparation of
8-Isopropyl-3,8-dimethyl-1H-imidazo-[1',2':1,2]pyrrolo[3,4 e]indole-6,9-dione and
8-isopropyl-3,8-dimethyl-1H-imidazo[2'1':5,1]pyrrolo-[3,4-e]indole-7,10-dione (1:1 mixture)

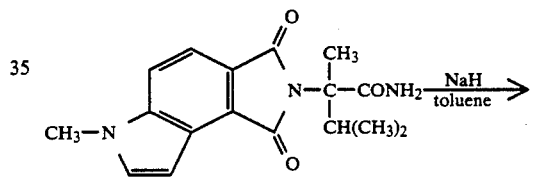

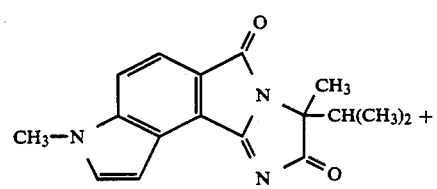

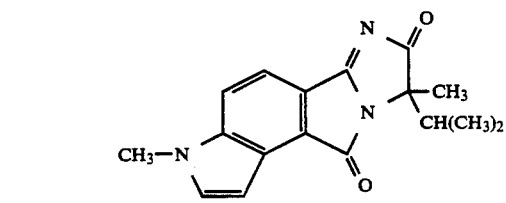

The 3,6-dihydro-a-isopropyl-a,6-dimethyl-1,3-dioxobenzo[1,2-b:3,4-c']dipyrrole-2(1H)acetamide (2.60 g, 8.30 mol) is added portionwise to a suspension of sodium hydride (0.800 g, 16.6 mol, 50% oil dispersion) in toluene at reflux temperature under a nitrogen atmosphere. After stirring for 20 hours at reflux temperature, the mixture is filtered hot through diatomaceous earth. The yellow filtrate is concentrated in vacuo to a dark yellow oil residue, which is triturated under ether to afford the title product mixture as a yellow solid (1.60 g, 65%), identified by $^1$HNMR spectroscopy.

EXAMPLE 54

Preparation of Methyl [5-(4-isopropyl-4-methyl-5-oxo-2-imidazolin-2-yl)-1-methyl]indole-4-carboxylate (I) and methyl [4-(4-isopropyl-4-methyl-5-oxo-2-imidazolin-2-yl)-1-methyl]indole-5-carboxylate (II)

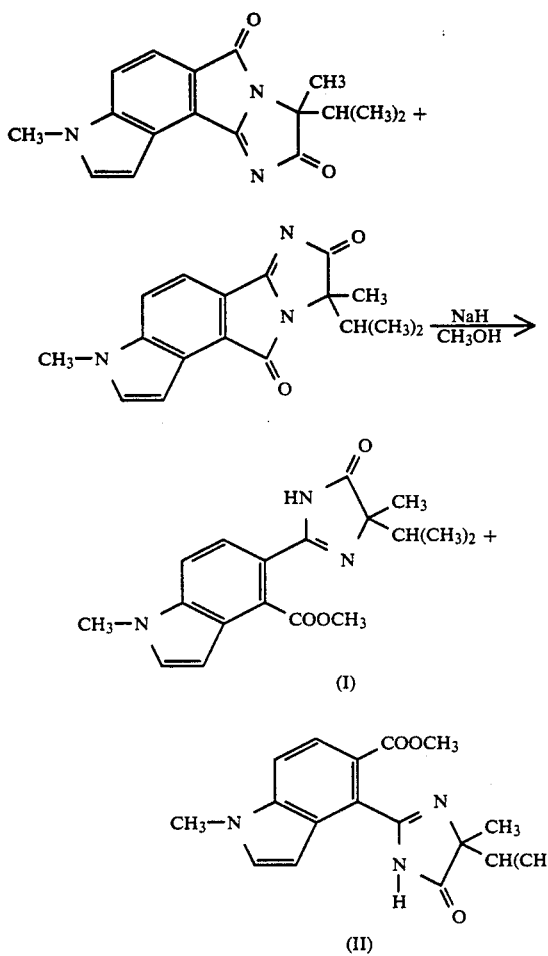

A catalytic amount of sodium hydride (60% oil dispersion) is added to a solution of a 1:1 mixture of 8-isopropyl-3,8-dimethyl-1H-imidazo[1',2':1,2]pyrrolo[3,4-e]indole-6,9-dione and 8-isopropyl-3,8-dimethyl-1H-imidazo[2'1':5,1]pyrrolo[3,4-e]indole-7,10-dione (1.00 g, 3.39 mmol) in methanol to pH 10. The reaction mixture is stirred for 1 hour at room temperature, treated with glacial acetic acid (2 drops) and concentrated in vacuo. The resultant residue is diluted with methylene chloride and water. The phases are separated and the organic phase is dried (MgSO₄) and concentrated in vacuo to give an orange foam, which is flash chromatographed (silica gel) to afford 3 fractions, which are in order of decreasing R$_f$:

1. title compound I, a pale-yellow solid (0.100 g);
2. a mixture of title compounds I and II (0.60 g);
3. title compound II, a pale-yellow solid (0.080 g).

The fractions are identified by ¹HNMR spectroscopy.

EXAMPLE 55

Preparation of 5-(4-Isopropyl-4-methyl-5-oxo-2-imidazolin-2-yl)-1-methylindole-4-carboxylic acid and 4-(4-isopropyl-4-methyl-5-oxo-2-imidazolin-2-yl)-1-methylindole-5-carboxylic acid ((1:1 mixture)

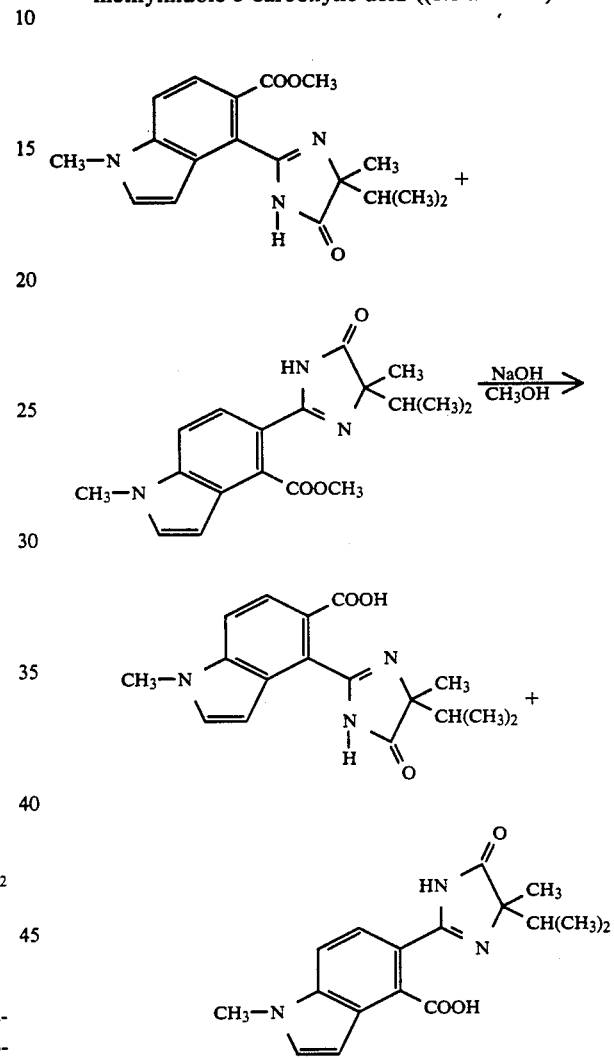

A mixture of 1.93N sodium hydroxide (0.70 mL, 1.34 mmol), a 1:1 mixture of methyl [5-(4-isopropyl-4-methyl-5-oxo-2-imidazolin-2-yl)-1-methyl]indole-4-carboxylate and methyl [4-(4-isopropyl-4-methyl-5-oxo-2-imidazolin-2-yl)-1-methyl]indole-5-carboxylate (0.400 g, 1.22 mmol) and methanol is stirred for 4 days at room temperature, and concentrated in vacuo. The resultant residue is diluted with water, cooled, acidified to pH 3 with concentrated hydrochloric acid, and extracted with ethyl acetate. The organic extracts are dried (MgSO₄) and concentrated in vacuo to afford the title product mixture as a solid (0.160 g, 41.9%), mp 266°-280° C., identified by ¹HNMR analysis.

EXAMPLE 56

Preparation of Dimethyl
1H-benzotriazole-4,5-dicarboxylate

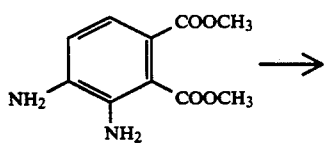

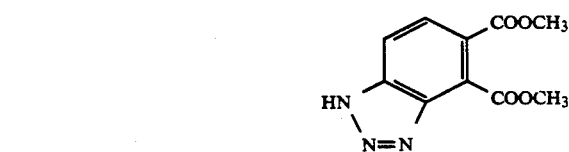

A stirred solution of methyl 3,4-diaminophthalate (2.24 g, 10 mmol) in acetic acid and methylene chloride is treated in a single portion with an ice cold solution of isoamylnitrile (1.6 mL) in 1 mL of methylene chloride at 5° C. The cooling bath is removed and the reaction mixture is allowed to exotherm to 40° C., subsequently heated at 80° C. for 30 minutes, cooled and concentrated in vacuo to give a brown oil residue. The residue is chromatographed using alumina E and 2-5% methanol in chloroform as eluent to yield the title product as a buff-colored solid, wt 0.73 g (31% yield), mp 147°-150° C.

EXAMPLE 57

Preparation of Dimethyl
1-methyl-1H-benzotriazole-4,5-dicarboxylate

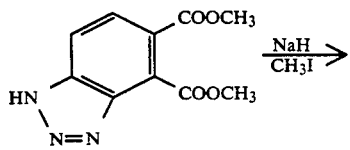

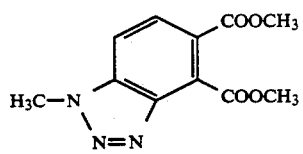

A stirred solution of dimethyl 1H-benzotriazole-4,5-dicarboxylate (10.1 g, 43 mmol) in dimethylformamide is treated portion-wise, with cooling, with sodium hydride. When gas evolution has ceased, the reaction mixture is treated dropwise with iodomethane (6.7 g, 46 mmol) stirred at room temperature for 2 hours, concentrated in vacuo and diluted with a mixture of chloroform and water. The layers are separated; the organic layer is washed with brine, dried over MgSO₄ and concentrated in vacuo to give a residue. The residue is chromatographed using silica gel and 35% ethyl acetate in hexanes to give the title product as a white solid, 3.15 g, mp 146°-147° C. The structure is determined by NMR NOE experiments.

EXAMPLE 58

Preparation of
4-(4-Isopropyl-4-methyl-5-oxo-2-imidazolin-2-yl)-1-methyl-1H-benzotriazole-5-carboxylic acid

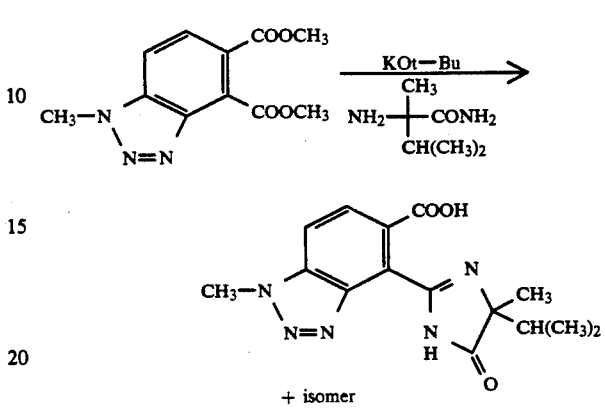

+ isomer

A mixture of dimethyl 1-methyl-1H-benzotriazole-4,5-dicarboxylate (0.73 g, 2.9 mmol) and a-methylvaliramide (0.40 g, 3.1 mmol) in toluene is treated portionwise with potassium tert-butoxide (0.68 g, 6.1 mmol) over a 30 minute period, heated at reflux temperature for 5 hours, allowed to cool to room temperature over a 16 hour period, treated with 5 mL of 2N sodium hydroxide and stirred for 1 hour. The phases are separated and the organic phase is extracted with water. The aqueous phases are combined, acidified to pH 3 with concentrated HCl, concentrated in vacuo to ½ the original volume, cooled to 5°-10° C. and filtered to give a 3:2 mixture of the title product and its regioisomer as a white solid, mp 140°-194° C.

The title product is isolated by flash chromatography to give a white solid, mp 250°-254° C. Structural analyses of the product 3:2 mixture and the isolated title product are determined using ¹H and ¹³CNMR spectral analysis.

EXAMPLE 59

Preemergence Herbicidal Evaluation of Test Compounds

The preemergence herbicidal activity of the imidazolinyl benzoheterocyclic compounds of the present invention is demonstrated by the following tests in which the seeds of a variety of monocotyledenous and dicotyledenous plant species are individually mixed with potting soil and planted on top of approximately one inch of soil in one pint cups. After planting, the cups are sprayed with an aqueous acetone solution containing the test compound. Said test solution consists of a 50/50 acetone/water mixture and a test compound in sufficient quantity to provide the equivalent of about 0.016 kg/ha to 4.0 kg/ha of active compound when applied to the soil through a spray nozzle operating at 40 psi for a predetermined time. The treated cups are then placed on greenhouse benches and cared for in accordance with conventional greenhouse procedures.

From 4 to 5 weeks after treatment, the test cups are evaluated and rated according to the rating system set forth below. The results of herbicide evaluations are expressed on a rating scale of 0-9. The scale is based upon a visual observation of plant stand, vigor, malformation, size, chlorosis and overall plant appearance as compared with a control.

The data obtained are recorded in Table I. Where more than one test is performed for a given compound, the average rating is shown.

| HERBICIDE RATING SCALE | | |
|---|---|---|
| Rating | Meaning | % Control Compared To Check |
| 9 | Complete kill | 100 |
| 8 | Approaching Complete Kill | 91–99 |
| 7 | Good Herbicidal Effect | 80–90 |
| 6 | Herbicidal Effect | 65–79 |
| 5 | Definite Injury | 45–64 |
| 4 | Injury | 30–44 |
| 3 | Moderate Effect | 16–29 |
| 2 | Slight Effect | 6–15 |
| 1 | Trace Effect | 1–5 |
| 0 | No Effect | 0 |

| PLANT SPECIES USED | | |
|---|---|---|
| Header Abb | Common Name | Scientific Name |
| Barnyardgr | Barnyardgrass | *Echinochloa crus-galli,* (L) Beau |
| Foxtail Sp | Foxtail Spp. | *Setaria* Spp. |
| P Nutsedge | Nutsedge, Purple | *Cyperus rotundus,* L. |
| Wild Oats | Oat, Wild | *Avena fatua,* L. |
| Quackgrass | Quackgrass | *Agropyron repens.* (L) Beauv. |
| Fld Bindwd | Bindweed, Field (Rhizome) | *Convolvulus arvensis,* L. |
| Mrnglry Sp | Morningglory Spp. | *Ipomoea* Spp. |
| Wild Mustd | Mustard, Wild | *Brassica kaber,* (DC) L. C. Wheelr |
| Velvetleaf | Velvetleaf | *Abutilon theophrasti,* Medic. |
| Sugarbeets | Sugarbeets | *Beta vulgaris,* L. |
| Soybean Br | Soybean, Bragg | *Glycine, max* (L) Men. CV Bragg |

TABLE I

Preemergence Herbicidal Evaluation Of Test Compounds

| Compound Name | Rate Kg/ha | Barny ardgr | Foxta il Sp | P Nut sedge | Wild Oats | Quack grass | Fld Bl ndwd | Mrngl ry Sp | Wild Mustd | Velve tleaf | Sugar beets | Soybe an Br |
|---|---|---|---|---|---|---|---|---|---|---|---|---|
| 1-Ethyl-4-(4-isopropyl-4-methyl-5-oxo-2-imidazolin-2-yl)-2-methyl-benzimidazole-5-carboxylic acid | .500 | 4 | 9 | 8 | 8 | 9 | 9 | 8 | 9 | 7 | 9 | 1 |
| | .125 | 2 | 9 | 4 | 3 | 9 | 9 | 7 | 8 | 6 | 7 | 4 |
| | .032 | 0 | 4 | 0 | 0 | 3 | 2 | 0 | 6 | 2 | 3 | 0 |
| 1-Methyl-4(and 5)-(4-isopropyl-4-methyl-5-oxo-2-imidazolin-2-yl)-1H-benzotriazole-5-(and 4)-carboxylic acid, 3:2 | .250 | 3 | 9 | 9 | 9 | 9 | 9 | 9 | 9 | 8 | 9 | 6 |
| | .063 | 0 | 2 | 9 | 0 | 9 | 9 | 8 | 8 | 7 | 9 | 3 |
| | .032 | 0 | 2 | 4 | 0 | 9 | 9 | 7 | 8 | 6 | 9 | 1 |
| | .016 | 0 | 2 | 2 | 0 | 2 | 7 | 4 | 6 | 6 | 8 | 0 |
| 1-Methyl-4-(4-isopropyl-4-methyl-5-oxo-2-imidazolin-2-yl)-2-(trifluoromethyl)-benzimidazole-5-carboxylic acid | .500 | 3 | 0 | 8 | 9 | 9 | 9 | 8 | 9 | 7 | 9 | 4 |
| | .250 | 0 | 0 | 7 | 2 | 9 | 9 | 8 | 9 | 5 | 4 | 1 |
| | .125 | 0 | 0 | 2 | 1 | 7 | 4 | 6 | 9 | 4 | 7 | 0 |
| | .063 | 0 | 0 | 2 | 0 | 7 | 4 | 6 | 9 | 6 | 2 | 0 |
| 1-Methyl-4-(4-isopropyl-4-methyl-5-oxo-2-imidazolin-2-yl)-1H-benzimidazole-5-carboxylic acid | .500 | 7 | 9 | 9 | 8 | 9 | 9 | 8 | 9 | 7 | 9 | 8 |
| | .250 | 3 | 9 | 9 | 8 | 9 | 9 | 8 | 9 | 7 | 9 | 8 |
| | .125 | 1 | 9 | 9 | 9 | 9 | 9 | 8 | 9 | 7 | 9 | 7 |
| | .032 | 0 | 3 | 8 | 4 | 9 | 7 | 7 | 9 | 6 | 9 | 3 |
| 1,2-Dimethyl-4-(4-isopropyl-4-methyl-5-oxo-2-imidazolin-2-yl)-benzimidazole-5-carboxylic acid | .500 | 9 | 9 | 9 | 9 | 9 | 9 | 9 | 9 | 8 | 9 | — |
| | .125 | 8 | 8 | 9 | 3 | 9 | 9 | 8 | 9 | 6 | 8 | — |
| | .063 | 7 | 8 | 4 | 0 | 9 | 9 | 1 | 9 | 6 | 7 | — |
| | .032 | 5 | 3 | 0 | 0 | 2 | 7 | 0 | 7 | 0 | 7 | — |
| Methyl 1,2-dimethyl-4-(4-isopropyl-4-methyl-5-oxo-2-imidazolin-2-yl)-benzimidazole-5-carboxylate | .500 | 6 | 6 | 2 | 4 | 2 | 2 | 7 | 3 | 2 | 4 | 0 |
| | .250 | 4 | 4 | 0 | 2 | 0 | 2 | 7 | 1 | 2 | 4 | 0 |
| | .125 | 2 | 2 | 0 | 0 | 0 | 2 | 4 | 0 | 0 | 6 | 0 |
| Methyl 1-ethyl-4-(4-isopropyl-4-methyl-5-oxo-2-imidazolin-2-yl)-2-methyl-benzimidazole-5-carboxylate | .500 | 0 | 0 | 2 | 2 | 6 | 9 | 7 | 2 | 2 | 8 | 0 |
| | .250 | 0 | 0 | — | 1 | 2 | 4 | 7 | 2 | 1 | 4 | 0 |
| | .125 | 0 | 0 | 0 | 0 | 2 | 4 | 2 | 2 | 0 | 2 | 0 |
| 1-Benzyl-4-(4-isopropyl-4-methyl-5-oxo-2-imidazolin-2-yl)-2-methyl-benzoimidazole-5-carboxylic acid | .500 | 0 | 0 | 2 | 2 | 9 | 9 | 7 | 9 | 3 | 8 | 3 |
| | .250 | 0 | 0 | 2 | 2 | 9 | 2 | 6 | 7 | 1 | 6 | 2 |
| | .125 | 0 | 0 | 0 | 1 | 7 | 0 | 4 | 7 | 0 | 4 | — |
| 1-Methyl-7(and 6)-(4-isopropyl-4-methyl-5-oxo-2-imidazolin-2-yl)-indole-6(and 7)carboxylic acid, 1:1 | .500 | 1 | 1 | 2 | 1 | 3 | 3 | 3 | — | 7 | 0 | — |
| | .250 | 1 | 1 | 0 | — | 2 | 4 | — | — | 5 | 0 | — |
| 1-Methyl-4-(4-isopropyl-4-methyl-5-oxo-2-imidazolin-2-yl)-benzimidazole-5-carboxylic acid | .500 | 9 | 9 | 9 | 9 | 9 | 9 | 9 | 9 | 8 | 9 | 6 |
| | .125 | 9 | 9 | 9 | 3 | 9 | 9 | 8 | 9 | 7 | 9 | 1 |
| | .063 | 9 | 9 | 9 | 2 | 9 | 9 | 2 | 9 | 6 | 9 | 0 |
| | .032 | 9 | 9 | 9 | 0 | 2 | 9 | 0 | 9 | 6 | 7 | 0 |
| 9-Isopropyl-2,3,9-trimethyl-imidazo[1',2':1,2]-pyrrolo[3,4-e]benzimidazole-6,8(3H,9H)dione | .500 | 9 | 9 | 9 | 7 | 9 | 9 | 8 | 9 | 8 | 9 | — |
| 1-Benzyl-4(and 5)-(4-isopropyl-4-methyl-5-oxo-2-imidazolin-2-yl)-5(and 4)-benzimidazolecarboxylic acid | .500 | 2 | — | 0 | 0 | 2 | 9 | 0 | 8 | 0 | 1 | 0 |
| | .250 | 0 | 2 | 0 | 0 | 0 | 1 | 0 | 8 | 0 | 0 | 0 |

EXAMPLE 61

Postemergence Herbicidal Evaluation of Test Compounds

The postemergence herbicidal activity of the imidazolinyl benzoheterocyclic compounds of the present invention is demonstrated by the following tests wherein a variety of monocotyledenous and dicotyledenous plants are treated with solutions of the test compound in aqueous acetone. Said test solutions consist of a 50/50 acetone/water mixture containing 0.5% TWEEN® 20, a polyoxyethylene sorbitan monolaurate surfactant manufactured by Atlas Chemical Industries and a test compound in sufficient quantity to provide the equivalent of about 0.016 kg/ha to 1.00 kg/ha of active compound when applied to the plants through a spray nozzle operating at 40 psi for a predetermined time. In the tests, seedling plants are grown in jiffy flats for about 2 weeks. The plants are sprayed with the test solution, placed on greenhouse benches and cared for in the usual manner commensurate with conventional greenhouse practice.

From 4 to 5 weeks after treatment, the plants are examined and rated according to the rating system described hereinabove. The herbicidal effectiveness of the compounds of the present invention is evident from the data recorded in Table II below.

When more than one test is performed for a given compound, the data are averaged.

| Header Abb | PLANT SPECIES USED Common Name | Scientific Name |
|---|---|---|
| Barnyardgr | Barnyardgrass | *Echinochloa crus-galli*, (L) Beau |
| Foxtail Sp | Foxtail Spp. | *Setaria* Spp. |
| P Nutsedge | Nutsedge, Purple | *Cyperus rotundus*, L. |
| Wild Oats | Oat, Wild | *Avena fatua*, L. |
| Quackgrass | Quackgrass | *Agropyron repens*, (L) Beauv. |
| Fld Bindwd | Bindweed, Field (Rhizome) | *Convolvulus arvensis*, L. |
| Mrnglry Sp | Morningglory Spp. | *Ipomoea* Spp. |
| Wild Mustd | Mustard, Wild | *Brassica kaber*, (DC) L. C. Wheelr |
| Velvetleaf | Velvetleaf | *Abutilon theophrasti*, Medic. |
| Sugarbeets | Sugarbeets | *Beta vulgaris*, L. |
| Soybean Br | Soybean, Bragg | *Glycine, max* (L) Men. CV Bragg |

TABLE II

Postemergence Herbicidal Evaluation Of Test Compounds

| Compound Name | Rate Kg/ha | Barny ardgr | Foxta il Sp | P Nut sedge | Wild Oats | Quack grass | Fld Bl ndwd | Mrngl ry Sp | Wild Mustd | Velve tleaf | Sugar beets | Soybe an Br |
|---|---|---|---|---|---|---|---|---|---|---|---|---|
| 1-Ethyl-4-(4-isopropyl-4-methyl-5-oxo-2-imidazolin-2-yl)-2-methyl-benzimidazole-5-carboxylic acid | .500 | 9 | 9 | 7 | 9 | 9 | 9 | 9 | 9 | 7 | 9 | 2 |
| | .250 | 8 | 8 | 4 | 9 | 9 | 9 | 9 | 9 | 6 | 9 | 3 |
| | .125 | 2 | 8 | 8 | 9 | 9 | 9 | 6 | 9 | 5 | 9 | 2 |
| | .063 | 2 | 8 | 2 | 7 | 9 | 9 | 4 | 9 | 2 | 9 | 2 |
| 1-Methyl-4(and 5)-(4-isopropyl-4-methyl-5-oxo-2-imidazolin-2-yl)-1H-benzotriazole-5-(and 4)-carboxylic acid, 3:2 | .250 | 8 | 9 | 9 | 9 | 9 | 9 | 8 | 9 | 9 | 9 | 8 |
| | .063 | 7 | 8 | 7 | 9 | 8 | 9 | 9 | 9 | 7 | 9 | 6 |
| | .016 | 4 | 6 | 4 | 2 | 7 | 9 | 7 | 8 | 2 | 6 | 2 |
| 1-Methyl-4-(4-isopropyl-4-methyl-5-oxo-2-imidazolin-2-yl)-2-(trifluoromethyl)-benzimidazole-5-carboxylic acid | 1.000 | 8 | 7 | 6 | 9 | 9 | 9 | 9 | 9 | 9 | 9 | 7 |
| | .500 | 7 | 6 | 6 | 9 | 8 | 9 | 9 | 7 | 7 | 9 | 4 |
| | .250 | 2 | 4 | 2 | 9 | 8 | 8 | 9 | 9 | 6 | 5 | 4 |
| | .125 | 2 | 2 | 2 | 8 | — | 9 | 8 | 9 | 2 | 2 | 2 |
| 1-Methyl-4-(4-isopropyl-4-methyl-5-oxo-2-imidazolin-2-yl)-1H-benzimidazole-5-carboxylic acid | .500 | 9 | 9 | 9 | 9 | 9 | 9 | 9 | 9 | 7 | 9 | 7 |
| | .250 | 7 | 9 | 8 | 9 | 9 | 9 | 8 | 9 | 7 | 9 | 6 |
| | .125 | 7 | 9 | 8 | 9 | 8 | 9 | 8 | 9 | 4 | 9 | 6 |
| | .063 | 6 | 7 | 7 | 9 | 8 | 5 | 8 | 8 | 4 | 9 | 6 |
| 1,2-Dimethyl-4-(4-isopropyl-4-methyl-5-oxo-2-imidazolin-2-yl)-benzimidazole-5-carboxylic acid | .500 | 9 | 9 | 7 | 9 | 9 | 9 | 9 | 9 | 8 | 9 | — |
| | .250 | 9 | 9 | 7 | 9 | 9 | 9 | 9 | 9 | 8 | 9 | — |
| | .125 | 9 | 9 | 5 | 9 | 9 | 9 | 9 | 9 | 7 | 9 | — |
| | .063 | 9 | 9 | 1 | 9 | 9 | 9 | 9 | 9 | 4 | 7 | — |
| Methyl 1,2-dimethyl-4-(4-isopropyl-4-methyl-5-oxo-2-imidazolin-2-yl)-benzimidazole-5-carboxylate | 1.000 | 6 | 7 | 0 | 0 | 3 | 9 | 7 | 8 | 0 | 3 | 3 |
| | .500 | 3 | 7 | 0 | 0 | 0 | 7 | 6 | 8 | 0 | 1 | 2 |
| | .250 | 2 | 7 | 0 | 0 | — | 7 | 6 | 3 | 0 | 1 | 1 |
| Methyl 1-ethyl-4-(4-isopropyl-4-methyl-5-oxo-2-imidazolin-2-yl)-2-methyl-benzimidazole-5-carboxylate | 1.000 | 2 | 7 | 0 | 0 | 4 | 9 | 7 | 8 | 0 | 4 | 3 |
| | .500 | 0 | 6 | 0 | 0 | 2 | 9 | 7 | 8 | 0 | 2 | 1 |
| | .125 | 0 | 2 | 0 | 0 | 0 | 6 | 4 | 2 | 0 | 1 | 0 |
| 1-Benzyl-4-(4-isopropyl-4-methyl-5-oxo-2-imidazolin-2-yl)-2-methyl-benzoimidazole-5-carboxylic acid | 1.000 | 2 | 2 | 2 | 0 | 9 | 9 | 7 | 9 | 2 | 9 | 3 |
| | .500 | 0 | 2 | 0 | 0 | 7 | 9 | 7 | 9 | 0 | 9 | 2 |
| | .250 | 0 | 1 | 0 | 0 | 2 | 9 | 8 | 8 | 0 | 9 | 2 |
| | .063 | 0 | 0 | 0 | 0 | 0 | 2 | 2 | 4 | 0 | 9 | 0 |
| 1-Methyl-4-(4-isopropyl-4-methyl-5-oxo-2-imidazolin-2-yl)-benzimidazole-5-carboxylic acid | .500 | 9 | 9 | 9 | 6 | 9 | 9 | 9 | — | 9 | 9 | 9 |
| | .125 | 9 | 9 | 9 | 6 | 9 | 9 | 9 | — | 9 | 9 | 4 |
| | .063 | 9 | 9 | 9 | 4 | 9 | 9 | 9 | — | 9 | 9 | 3 |
| | .032 | 9 | 9 | 8 | 2 | 9 | 9 | 8 | — | 4 | 9 | 2 |
| 9-Isopropyl-2,3,9-trimethyl-imidazo[1',2':1,2]-pyrrolo[3,4-e]benzimidazole-6,8(3H,9H)dione | .500 | 9 | 9 | 7 | 9 | 9 | 9 | 9 | — | 6 | 9 | — |
| | .250 | 9 | 9 | 4 | 9 | 9 | 9 | 9 | — | 7 | 9 | — |
| | .125 | 7 | 9 | 2 | 4 | 8 | 8 | 9 | — | 5 | 9 | — |
| | .063 | 9 | 9 | 0 | 3 | 9 | 9 | 9 | — | 0 | 9 | — |
| 1-Benzyl-4(and 5)-(4-isopropyl-4-methyl-5-oxo-2-imidazolin-2-yl)benzimida- | .063 | 0 | 1 | 0 | 7 | 8 | 0 | 0 | 8 | 0 | 2 | 0 |
| | .032 | 0 | 0 | 0 | 4 | 2 | 0 | 0 | 4 | 0 | 2 | 0 |

TABLE II-continued

| | | Postemergence Herbicidal Evaluation Of Test Compounds | | | | | | | | | |
|---|---|---|---|---|---|---|---|---|---|---|---|
| Compound Name | Rate Kg/ha | Barny ardgr | Foxta il Sp | P Nut sedge | Wild Oats | Quack grass | Fld Bl ndwd | Mrngl ry Sp | Wild Mustd | Velve tleaf | Sugar beets | Soybe an Br |
| zole-5(and 4)-carboxylic acid, 1:1 | | | | | | | | | | | | |

What is claimed is:

1. A compound having the structure

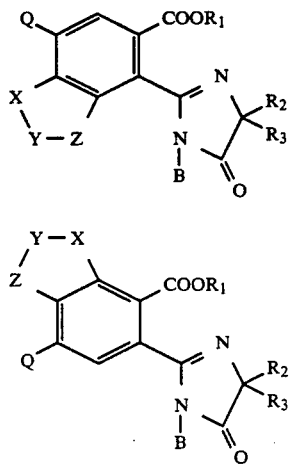

wherein $R_1$ is hydrogen, di($C_1$-$C_4$) alkylimino;

$C_1$-$C_{12}$ alkyl optionally substituted with one or more of the following: $C_1$-$C_4$ alkoxy, $C_1$-$C_4$ alkylthio, halogen, hydroxy, $C_3$-$C_6$ cycloalkyl, benzyloxy, furyl, phenyl, halophenyl, $C_1$-$C_4$ alkylphenyl, $C_1$-$C_4$ alkoxyphenyl, nitrophenyl, carboxy, $C_1$-$C_4$ alkoxycarbonyl, cyano or tri($C_1$-$C_4$)alkylammonium halide;

$C_3$-$C_{12}$ alkenyl optionally substituted with one or more of the following groups: $C_1$-$C_4$ alkoxy, phenyl, halogen or $C_1$-$C_4$ alkoxycarbonyl, $C_3$-$C_6$ cycloalkyl optionally substituted with one or more $C_1$-$C_4$ alkyl groups, $C_3$-$C_{16}$ alkynyl optionally substituted with one or more $C_1$-$C_4$ alkyl groups; or a cation;

$R_2$ is $C_1$-$C_4$ alkyl;

$R_3$ is $C_1$-$C_4$ alkyl or $C_3$-$C_6$ cycloalkyl; and when $R_2$ and $R_3$ are taken together with the carbon to which they are attached they may represent $C_3$-$C_6$ cycloalkyl optionally substituted with methyl;

B is hydrogen, $COR_4$ or $SO_2R_5$ with the proviso that when B is $COR_4$ or $SO_2R_5$, $R_1$ is other than hydrogen or a cation and $R_9$ is other than hydrogen;

$R_4$ is $C_1$-$C_{11}$ alkyl, chloromethyl or phenyl optionally substituted with halogen, nitro or $C_1$-$C_4$ alkyl;

$R_5$ is $C_1$-$C_4$ alkyl or phenyl optionally substituted with $C_1$-$C_4$ alkyl;

X, Y and Z are each independently N, or $NR_9$;

the ⚌ configuration represents either a single bond or a double bond with the proviso that when any of X, Y or Z is $CR_7R_8$ or $NR_9$, then the ⚌ configuration represents a single bond and with the further proviso that at least one of the ⚌ configuration represents a single bond;

$R_6$, $R_7$ and $R_8$ are independently hydrogen, halogen, $C_1$-$C_4$ alkoxy or $C_1$-$C_4$ alkyl optionally substituted with one hydroxy or one to three halogens, $C_1$-$C_4$ alkoxy groups or $C_1$-$C_4$ alkylthio groups;

$R_9$ is hydrogen or $C_1$-$C_4$ alkyl optionally substituted with one hydroxy or one to three halogens, $C_1$-$C_4$ alkoxy groups or $C_1$-$C_4$ alkylthio groups;

Q is hydrogen, halogen $C_1$-$C_4$ alkoxy or $C_1$-$C_4$ alkyl optionally substituted with one to three of the following: halogen, $C_1$-$C_4$ alkoxy, $C_1$-$C_4$ alkylthio, or $C_2$-$C_4$ alkenyl;

the optical isomers thereof when $R_2$ and $R_3$ are not the same or when $R_6$ and $R_7$ are not the same;
the tautomers and geometric isomers thereof are the agriculturally acceptable acid addition salts thereof except when $R_1$ is a salt-forming cation.

2. The compound according to claim 1 wherein $R_1$ is hydrogen or a cation; $R_2$ is methyl; $R_3$ is isopropyl and B and Q are hydrogen.

3. The compound according to claim 1 wherein X, Y and Z are independently N or $NR_9$.

4. The compound according to claim 3 wherein X is $NR_9$ and Y and Z are N.

5. The compound according to claim 4 wherein said compound has the structure a.

6. The compound according to claim 5, 1-methyl-4-(4-isopropyl-4-methyl-5-oxo-2-imidazolin-2-yl)-1H-benzotriazole-5-carboxylic acid.

7. The method for the control of monocotyledonous and dicotyledonous plant species which comprises applying to the foliage of said plant species or to the soil or water containing seeds or other propagating organs of said plant species a herbicidally effective amount of a compound having the structure as described in claim 1.

8. The method according to claim 7 wherein X is $NR_9$ and Y and Z are N.

9. The method according to claim 7 wherein the compound is applied to the foliage of said plant species or to the soil or water containing seeds or other propagating organs of said plant species at a rate of about 0.016 kg/ha to 4.0 kg/ha.

10. A herbicidal composition which comprises an inert solid or liquid diluent and a herbicidally effective amount of a compound having the structure as described in claim 1.

11. The herbicidal composition according to claim 10 wherein the compound has the structure as described in claim 4.

* * * * *